United States Patent
Maher et al.

(10) Patent No.: US 11,457,614 B2
(45) Date of Patent: Oct. 4, 2022

(54) ANIMAL HARNESS SECURITY SYSTEMS AND METHODS

(71) Applicant: VetMeasure, Inc., Ames, IA (US)

(72) Inventors: Kevin D. Maher, Ames, IA (US); Joel Adrian Moritz, Jr., Fort Collins, CO (US); Dennis Matthew Schultz, Fort Collins, CO (US)

(73) Assignee: VetMeasure, Inc., Ames, IA (US)

( * ) Notice: Subject to any disclaimer, the term of this patent is extended or adjusted under 35 U.S.C. 154(b) by 83 days.

(21) Appl. No.: 16/937,418

(22) Filed: Jul. 23, 2020

(65) Prior Publication Data

US 2020/0359605 A1    Nov. 19, 2020

Related U.S. Application Data

(63) Continuation-in-part of application No. 16/550,201, filed on Aug. 24, 2019.

(Continued)

(51) Int. Cl.
*A01K 29/00* (2006.01)
*A01K 27/00* (2006.01)
(Continued)

(52) U.S. Cl.
CPC .......... *A01K 29/005* (2013.01); *A01K 27/002* (2013.01); *A01K 27/008* (2013.01);
(Continued)

(58) Field of Classification Search
CPC .. A01K 29/005; A01K 27/002; A01K 27/008; G08B 21/182; G06K 2009/00939
See application file for complete search history.

(56) References Cited

U.S. PATENT DOCUMENTS 5,372,125 A    12/1994  Lyons
8,830,068 B2    9/2014  Campbell et al.
(Continued)

FOREIGN PATENT DOCUMENTS

CN    110996656 A  *  4/2020  ............ A01K 27/00
RU    2454924 C2    7/2012
(Continued)

OTHER PUBLICATIONS

PCT/US2019/048048 International Search Report and Written Opinion dated Dec. 5, 2019, 7 pp.
(Continued)

*Primary Examiner* — Joshua D Huson
*Assistant Examiner* — Alanna K Peterson
(74) *Attorney, Agent, or Firm* — Lathrop GPM LLP

(57) ABSTRACT

A system and associated methods use an animal harness attached to an animal to improve security at a location (e.g., a home, office, warehouse, etc.). The animal harness collects health status data of the animal, and the health status data is processed using one or more algorithms that detect changes in one or more of excitement, agitation, stress, and/or anxiety in the animal. These changes are interpreted, using a behavioral model of the animal, to determine whether the animal is witnessing a security event at the location, and when the health status data indicates the security event, the system may generate an alert. The behavioral model may be updated over time to improve performance of the algorithms to detect security events.

12 Claims, 22 Drawing Sheets

Related U.S. Application Data

(60) Provisional application No. 62/722,508, filed on Aug. 24, 2018.

(51) Int. Cl.
| | | |
|---|---|---|
| *G08B 21/18* | (2006.01) | |
| *G06V 40/10* | (2022.01) | |
| *A61B 5/00* | (2006.01) | |
| *A61B 5/16* | (2006.01) | |
| *A61B 5/0205* | (2006.01) | |
| *A61B 5/024* | (2006.01) | |
| *A61B 5/08* | (2006.01) | |
| *A61B 5/11* | (2006.01) | |
| *A61B 7/00* | (2006.01) | |
| *A61B 5/282* | (2021.01) | |

(52) U.S. Cl.
CPC .......... *A01K 27/009* (2013.01); *A61B 5/0022* (2013.01); *A61B 5/02055* (2013.01); *A61B 5/165* (2013.01); *A61B 5/6831* (2013.01); *A61B 5/746* (2013.01); *G08B 21/182* (2013.01); *A61B 5/02438* (2013.01); *A61B 5/0816* (2013.01); *A61B 5/11* (2013.01); *A61B 5/282* (2021.01); *A61B 7/00* (2013.01); *A61B 2503/40* (2013.01); *A61B 2560/0252* (2013.01); *A61B 2562/029* (2013.01); *A61B 2562/164* (2013.01); *G06V 40/15* (2022.01)

(56) References Cited

U.S. PATENT DOCUMENTS

| 9,823,138 | B2 | 11/2017 | Zakharov et al. |
|---|---|---|---|
| 10,041,843 | B2 | 8/2018 | Zakharov et al. |
| 2005/0197546 | A1* | 9/2005 | Mardiks ................ A61B 5/746 |
| | | | 600/300 |
| 2007/0078324 | A1 | 4/2007 | Wijisiriwardana |
| 2013/0046219 | A1 | 2/2013 | Mendez et al. |
| 2013/0171599 | A1 | 7/2013 | Bleich et al. |
| 2015/0005609 | A1 | 1/2015 | Evans et al. |
| 2016/0165852 | A1* | 6/2016 | Goldfain .............. A61B 5/6831 |
| | | | 340/573.3 |
| 2018/0184735 | A1 | 7/2018 | Longinotti-Buitoni et al. |
| 2018/0263220 | A1* | 9/2018 | Schab ................ G08B 21/182 |
| 2019/0200577 | A1 | 7/2019 | Kath |
| 2019/0254599 | A1* | 8/2019 | Young .................. A61B 5/1118 |
| 2019/0261599 | A1* | 8/2019 | Bedell ................ A01K 11/008 |
| 2020/0090821 | A1* | 3/2020 | Lai ........................ G16H 10/60 |
| 2020/0178495 | A1* | 6/2020 | Womble ............... A01K 5/0114 |

FOREIGN PATENT DOCUMENTS

| RU | 2601153 C2 | 10/2016 | |
|---|---|---|---|
| RU | 2645930 C2 | 2/2018 | |
| WO | WO 2006/113804 A2 | 10/2006 | |
| WO | WO 2016110804 A1 | 7/2016 | |
| WO | WO 2017/064158 A1 | 4/2017 | |
| WO | WO-2019143714 A1 * | 7/2019 | ............. G16H 30/40 |

OTHER PUBLICATIONS

U.S. Appl. No. 16/550,201 Non-Final Office Action dated Jan. 6, 2022, 11 pages.

U.S. Appl. No. 16/550,201 Final Office Action dated Jun. 15, 2022, 12 pages.

* cited by examiner

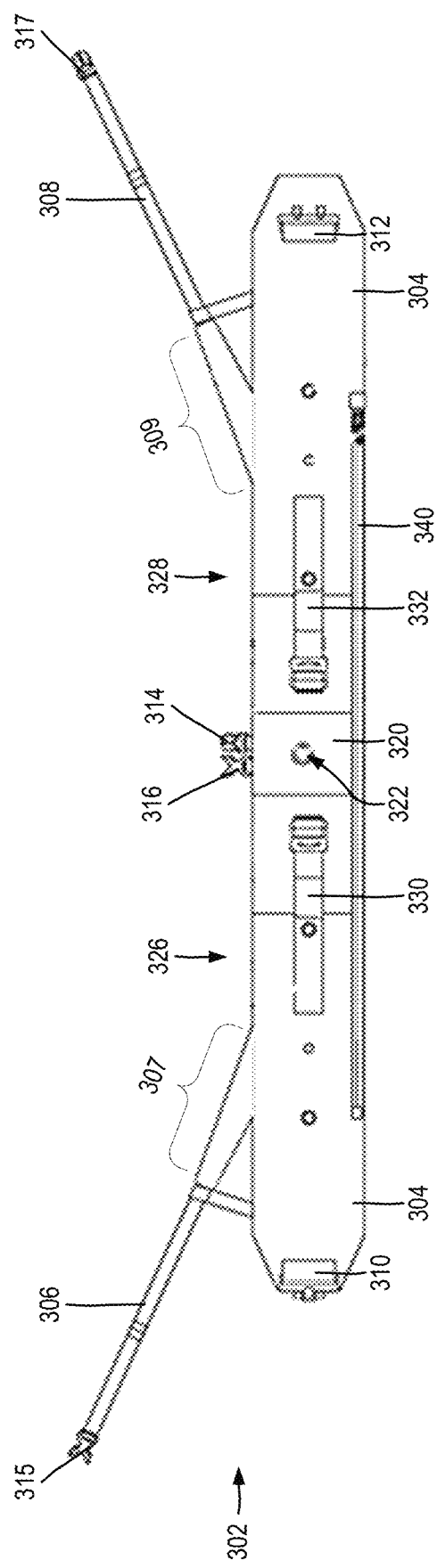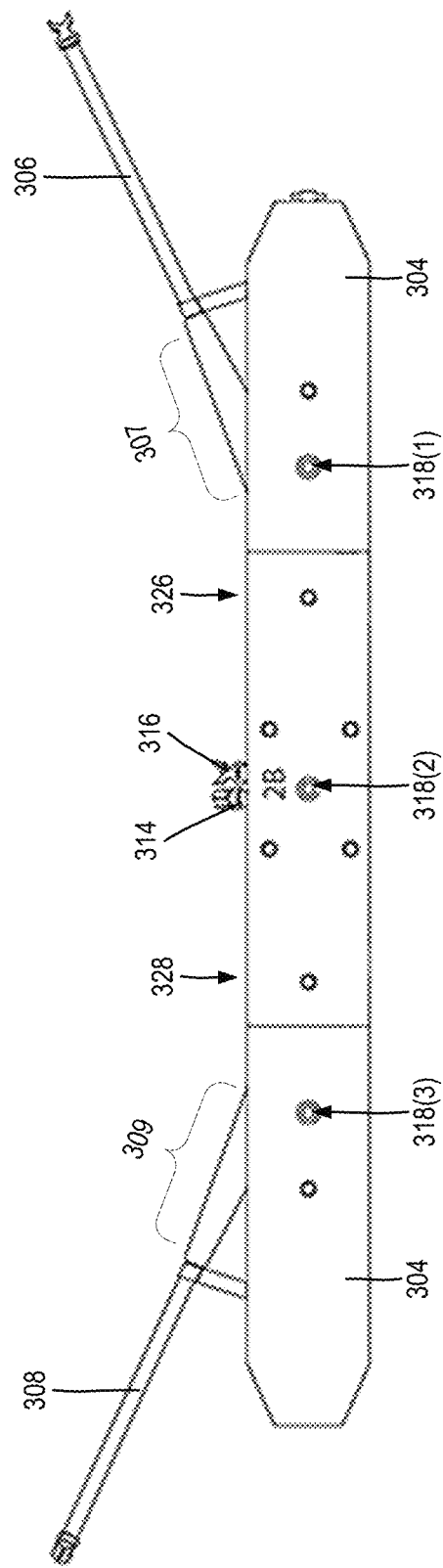

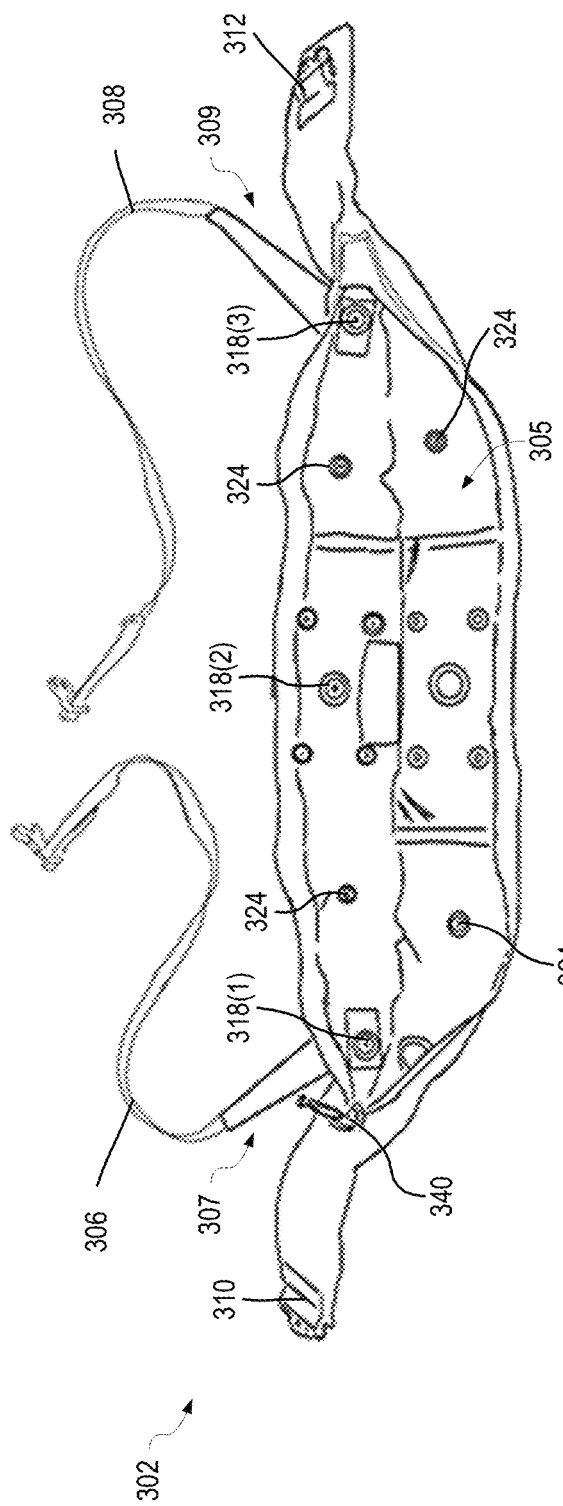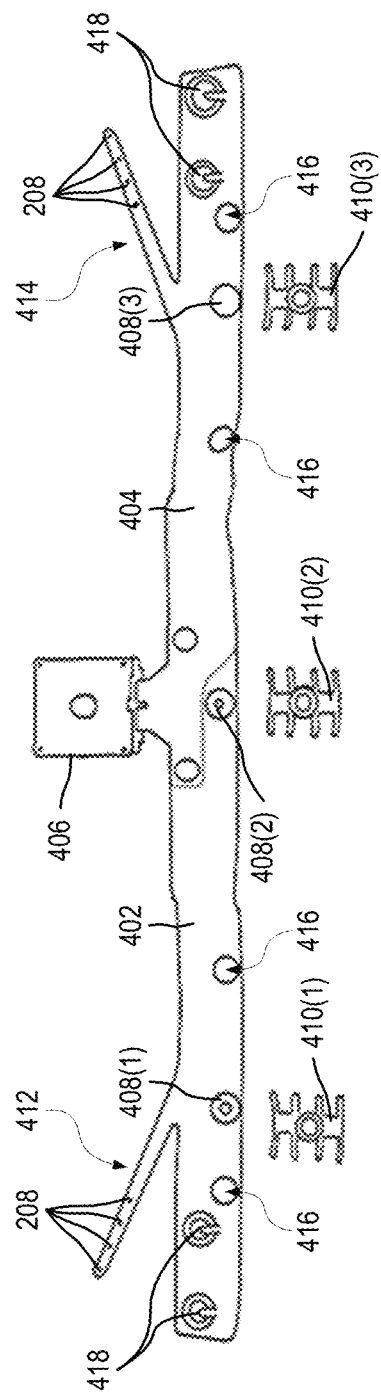

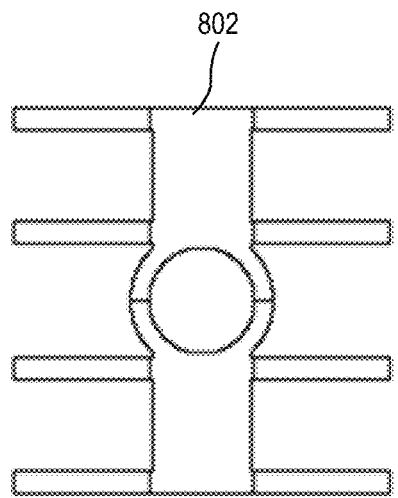 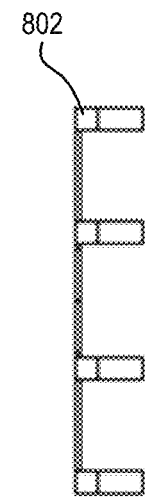
Figure 11A    Figure 11B
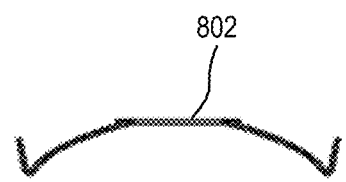 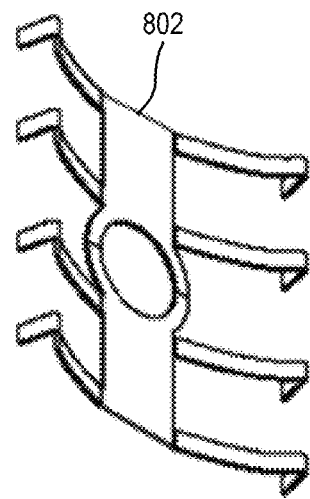
Figure 11C    Figure 11D

ANIMAL HARNESS SECURITY SYSTEMS AND METHODS

RELATED APPLICATION

This application is a continuation-in-part of U.S. patent application Ser. No. 16/550,201, titled "Round-the-Clock Monitoring of an Animal's Health Status," filed Aug. 24, 2019, which claims priority to U.S. Provisional Patent Application Ser. No. 62/722,508, titled "Round-The-Clock Monitoring of An Animal's Health Status," filed Aug. 24, 2018. Each of these applications is incorporated in its entirety herein by reference.

FIELD OF THE INVENTION

Security based upon electronic equipment mounted on an animal.

BACKGROUND

Dogs are frequently used to improve security at a property. A dog barking is a deterrent for a person intending to break-in to a property. An animal at a property is, however, problematic to security devices installed at the property. The animal often unwantedly triggers the alarm when moving around. An owner of the property, when faced with unwanted triggering of the alarm system by the animal, often disables one or more sensors of the alarm system, and/or opts to not arm the alarm system at all.

SUMMARY

On aspect of the present embodiments includes the realization that an animal at a property may unwantedly trigger an intruder alarm installed at the property. The present embodiments solve this problem by providing an animal harness that attaches to the animal. When the intruder alarm is triggered, it communicates with the animal harness to determine whether the animal caused the trigger, and when the animal harness indicates that the animal is active and near a sensor of the intruder alarm, the trigger is ignored. Advantageously, the animal harness accurately determines the animal's activity and informs the intruder alarm when the trigger is caused by the animal.

Another aspect of the present embodiments includes the realization that sensors of an intruder alarm are not as acute as senses of an animal. The present embodiments solve this problem by providing an animal harness that attaches to an animal and detects activity and emotional state of the animal. When the detected activity and/or emotional state indicates that an unknown person is attempting to enter a property, the animal harness triggers an intruder alarm. Advantageously, by detecting the emotional state of the animal, the animal's senses may be used to increase sensitivity of the intruder alarm.

Another aspect of the present embodiments includes the realization that by making the animal harness an IoT device, that information collected by the animal harness may be used by other equipment, such as a security apparatus. The present embodiments solve this problems by wirelessly capturing health status data from an animal harness attached to an animal at a location (e.g., a home, an office, a warehouse, etc.) and processing the health status data to learn additional information.

The purpose of this new monitor system (e.g., also known as MeasureON! harness & VetMeasure app) is to be utilized by veterinarians, veterinary technicians, animal owners, livestock producers, animal caretakers, animal trainers and handlers, and others to monitor the health metrics and environmental conditions of an animal of all species, including humans. The initial target customer is the innovative veterinarian, who may incorporate this new monitor system into a veterinary practice to monitor high risk patients, specifically during the surgery and post-surgical recovery periods. The new monitor system may be sent home with the patient for continuous at-home monitoring to establish an accurate baseline for return visits, as well as to ensure recovery is occurring on schedule and the owner is complying with veterinarian recommendations. The system may include a wearable monitoring device containing many sensors and capabilities, or discreet monitoring and measurement equipment.

This new monitor system helps prevent heat stroke and/or heat stress in an animal by providing real-time analysis of the animal's body temperature and environmental conditions. The new monitor system also measures pulse/heart rate, ECG, respiratory rate, and activity level of the animal. The system also monitors the temperature and relative humidity level in the immediate vicinity of the animal. All these features combined generate an individual health profile for the animal which aids the veterinarian and/or animal owner/caretaker in diagnosis and/or treatment for health-related concerns.

In one embodiment, an animal harness security system includes an animal harness and a server. The animal harness includes: an electronics module with at least one first processor, first memory storing firmware, and a wireless transceiver; a plurality of sensors; at least one flexible panel electrically coupling the plurality of sensors to the electronics module; a soft chassis having a main body with a cavity for containing and positioning the flexible panel around a heart girth of an animal, wherein the soft chassis positions the sensors around the animal to detect health characteristics of the animal; and at least three snap connectors, a female side of each one of the three snap connectors being attached to a different one of three removable ECG electrodes, and a male side of each one of the three snap connectors being attached through one of three holes in the flexible panel and electrically connected, through the flexible panel, to the electronics module, wherein each of the three snap connectors are assembled through three holes in the soft chassis to position the three removable ECG electrodes at a left side of the animal, a right side of the animal, and on a back of the animal. The server includes: at least one second processor; and a second memory storing machine readable instructions that, when executed by the at least one second processor, cause the at least one second processor to: receive, at intervals, health status data from the animal harness; determine whether the health status data indicates that the animal is witnessing a security event; and generating an alarm signal to indicate the security event.

In another embodiment, a security-enhanced animal harness includes: an animal harness sized to attach around a heart girth of an animal at a location, and including: a plurality of sensors for sensing health characteristics of the animal; a wireless transceiver; a processor; and a memory storing firmware having machine readable instructions that when executed by the processor, cause the processor to: read, at intervals, the plurality of sensors to collect health status data of the animal; process the health status data to detect changes in behavior of the animal indicative of the animal witnessing a security event at the location; and send, via the wireless transceiver, a message indicative of the security event to a gateway connected to the Internet.

In another embodiment, a method for detecting a security event witnessed by an animal, includes: capturing, at intervals, from a plurality of sensors positioned on the animal by an animal harness worn by the animal, health status data of the animal; processing the health status data to detect changes in at last one of excitement, agitation, stress, and anxiety in the animal; interpreting the changes in the at least one of excitement, agitation, stress, and anxiety to determine whether the animal is witnessing the security event; and sending an event signal indicative of the security event to a security apparatus when the animal is witnessing the security event.

BRIEF DESCRIPTION OF THE DRAWINGS

FIGS. 3A and 3B are schematic diagrams illustrating an outside and an inside, respectively, of a soft chassis that forms the physical structure of the animal harness of FIGS. 1 and 2, in embodiments.

FIG. 3C is a perspective view of the opened soft chassis of FIGS. 3A and 3B, in embodiments.

FIG. 4 shows flexible panels and an electronics module that may be inserted into the soft chassis of FIG. 3C, in embodiments.

FIGS. 11A-11D show top, side, end, and perspective views, respectively, of the comb-style ECG electrode of FIGS. 4, 8, and 10, in embodiments.

DETAILED DESCRIPTION OF INVENTION

Animal Health Monitoring System

Figure 1:
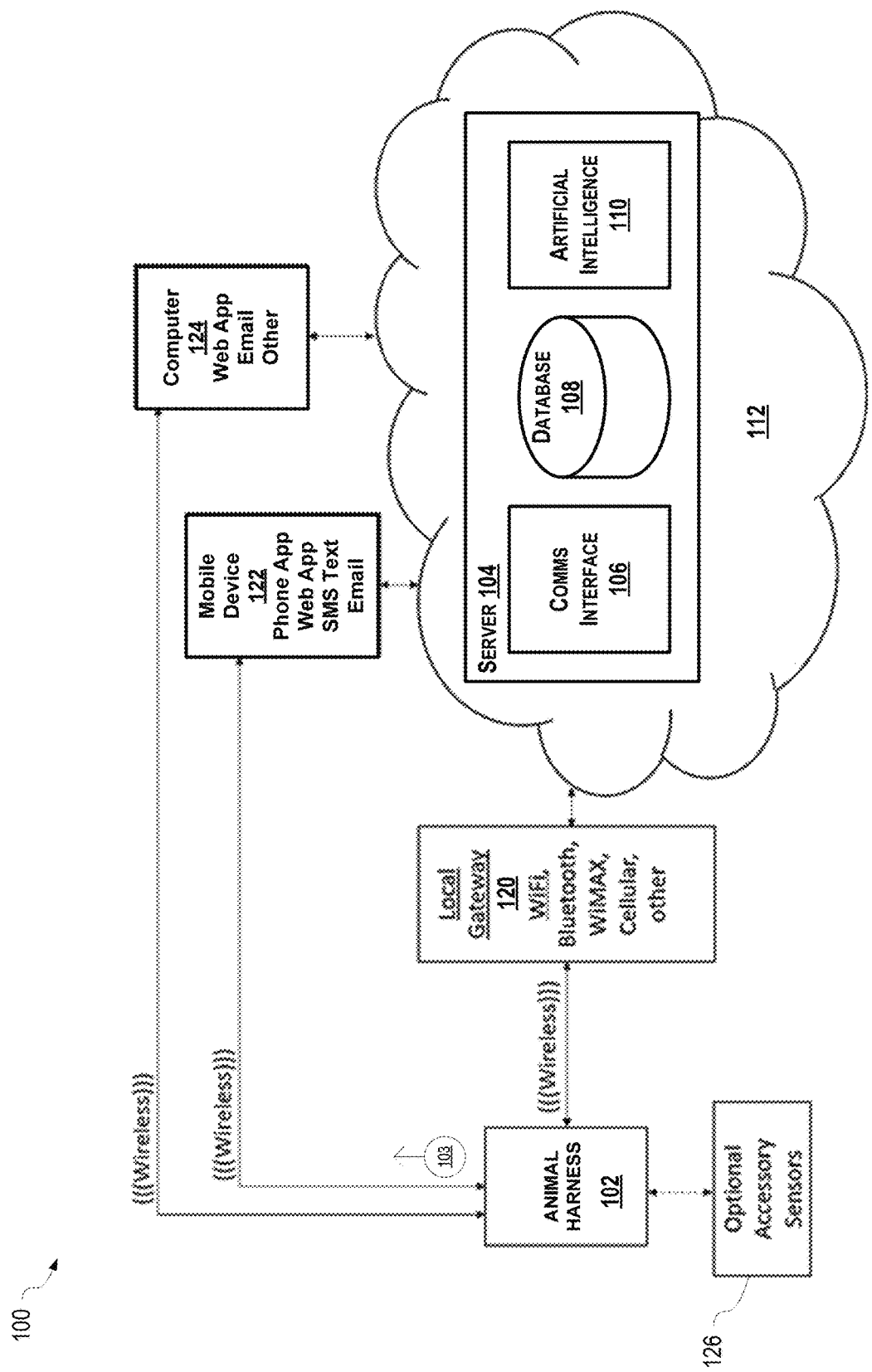
FIG. 1 is a block diagram showing one example animal health monitoring system, in embodiments.

FIG. 1 is a block diagram showing one example animal health monitoring system 100 that monitors an animal's health status round-the-clock (e.g., continuously). System 100 may also be referred to as the VetMeasure system. System 100 includes an animal harness 102 that attaches around a heart girth of the animal and straps in front of the chest to surround the thoracic region to measure, at intervals, health measurements that may include one or more of animal body temperature, animal pulse/heart rate, animal respiration rate, animal activity level, environmental temperature, and environmental humidity. System 100 also includes at least one remote server 104 that may receive the health measurements (shown as health status data 103) from animal harness 102. Although shown as a single message, different parts of health status data 103 may be sent to each of server 104 and/or mobile device 122 at different rates, as described in detail below. Server 104 is a digital computer operating within "the cloud" 112 and that is accessible via the Internet for example. Server 104 may include a communication interface 106, a database 108, and artificial intelligence and diagnostics module 110 that cooperate to receive, store, and evaluate measurement data from animal harness 102. Communication interface 106 may implement one or more of Internet services, email, short-message-service (SMS), and so on. Database 108 may store health status data 103 received from animal harness 102. AI and diagnostics module 110 may evaluate database 108 and received health status data 103 to determine a health status of the animal.

Animal harness 102 may communicate wirelessly with server 104 via one or more of a local gateway 120 (e.g., a Wi-Fi access point), a mobile device 122 (e.g., a user's smartphone), and another computer 124 (e.g., a laptop or desktop computer). Animal harness 102 may implement at least one wireless protocol, such as Wi-Fi, WiMAX, cellular, Z-wave, Bluetooth, and so on, and may thereby communicate with server 104 via one or more of local gateway 120, mobile device 122, and computer 124. Animal harness 102 may also couple with other optional accessory sensors 126 that may operate as stand-alone devices. Mobile device 122 may run an application (e.g., an app) that allows a user to wirelessly interact with animal harness 102, such as for configuration, viewing data, and so on. Communication interface 106 may implement a web interface (e.g., a web site and/or portal) that allows an authorized user to interact with server 104 to view data stored in database 108 for example, and/or to configure and/or use AI and diagnostics module 110 to evaluate health status data 103 as it is received and/or stored in database 108. Server 104, communication interface 106, and/or AI and diagnostics module 110 may provide other tools for viewing and/or processing health status data 103. Server 104 may use other methods for communication with animal harness 102 and/or the user without departing from the scope hereof.

Animal Harness

Figure 2:
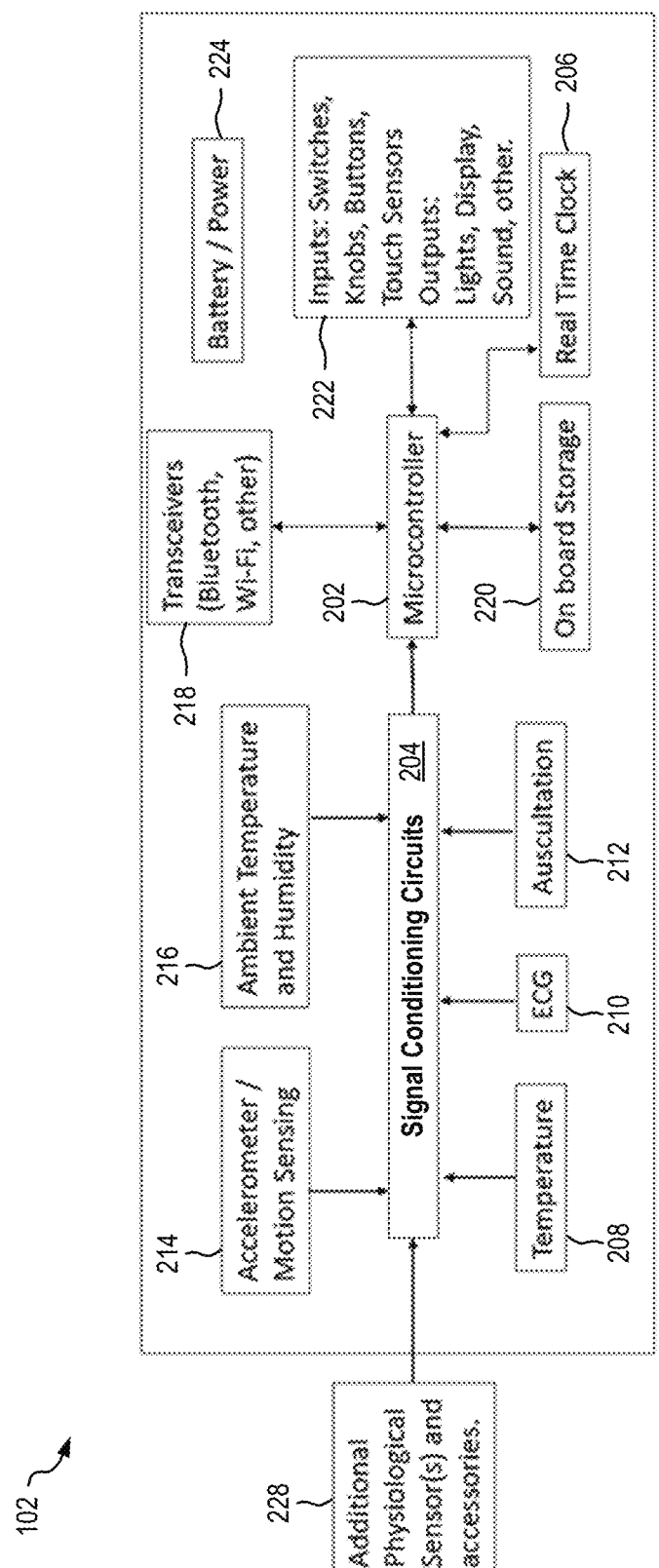
FIG. 2 is a block diagram showing the animal harness of FIG. 1 in further example detail, in embodiments.

FIG. 2 is a block diagram showing animal harness 102 of FIG. 1 in further example detail. Animal harness 102 may include a microcontroller 202 that has at least one processor and memory storing machine readable instructions that, when executed by the processor control the processor to implement the functionality of the animal harness 102 as described herein. Animal harness 102 includes a real-time clock 206 that maintains a current time of day, which may be used to denote a time when a measurement was taken.

Animal harness 102 includes a plurality of sensors including one or more of a temperature sensor 208, an ECG sensor 210, an auscultation sensor 212, an accelerometer/motion sensor 214 (e.g., accelerometer), and ambient temperature and humidity sensor 216 (e.g., ambient temperature and ambient humidity). Sensors 208, 210, 212, 214, and 216, are built into animal harness 102 and may be electrically coupled with signal conditioning circuits 204 that may implement one or more of filtering, amplifying, and analog to digital conversion. Microcontroller 202 processes signals from sensors 208, 210, 212, 214, and 216, and may transmit the information as sensor health status data 103 via a transceiver 218 (e.g., using one or more protocols selected from the group comprising Bluetooth, Wi-Fi, and cellular networks, 2, 3, 4, and 5g data networks) included with animal harness 102.

Sensor health status data 103 may include an identifier that uniquely identifies one or both of animal harness 102 and/or the animal wearing the harness, and may include data from one or more of sensors 208, 210, 212, 214, and 216, (e.g., a body temperature, ECG measurement, movement measurement, and so on), each tagged with a time that the sensor measurement was taken. When a connection to remote server 104 is unavailable, microcontroller 202 may store the sensor data and corresponding time in an onboard storage 220 (e.g., a non-volatile memory) of animal harness 102 for later transmission. In certain embodiments, animal harness 102 may send (e.g., via Bluetooth and/or Wi-Fi) health status data 103 to mobile device 122 and/or computer 124 where it may be displayed in real time (e.g., as a graph or other type of visual output).

Animal harness 102 may also include a user interface 222 that allows a user to interact directly (as opposed to using mobile device 122 for example) with animal harness 102. User interface 222 may include one or more input devices, such as switches, knobs, buttons, and touch sensors, and one or more output devices, such as lights, a display, audio (e.g., a sound generator, a piezoelectric element) and so on. Animal harness 102 also include an electrical power store 224 (e.g., a battery) that powers components of animal harness 102. As noted above, one or more additional physiological sensors 228 may be communicatively coupled (e.g., wired and/or wirelessly) with animal harness 102 and their data processed, stored, and/or transmitted within health status data 103.

Physical Harness

FIGS. 3A and 3B are schematic diagrams illustrating an outside and an inside, respectively, of a soft chassis 302 that forms the physical structure of the animal harness 102 of FIGS. 1 and 2. FIG. 3C is a perspective view of the soft chassis 302 of FIGS. 3A and 3B with a zipper 340 opened and with flexible panels removed. FIG. 4 shows flexible panels 402 and 404 and an electronics module 406 that may be inserted into the soft chassis 302 of FIG. 3C. FIGS. 3A, 3B, 3C and 4 are best viewed together with the following description. Although shown as two flexible panels, flexible panels 402 and 404 may be formed as a single panel without departing from the scope hereof.

Soft chassis 302 is formed of fire-retardant materials and includes a main body 304 that is essentially one long hollow strap or tube that is sized to passes around the girth of the animal and joins together using clasps 310 and 312 positioned at opposite ends of main body 304. Soft chassis 302 has two adjustable length axillary straps 306 and 308 that are positioned and sized to pass around right and left forelegs, respectively, of the animal, crossing in front and connecting, at distal ends, to connectors 314 and 316, respectively, of main body 304 to secure animal harness 102 onto the animal.

Figure 10:
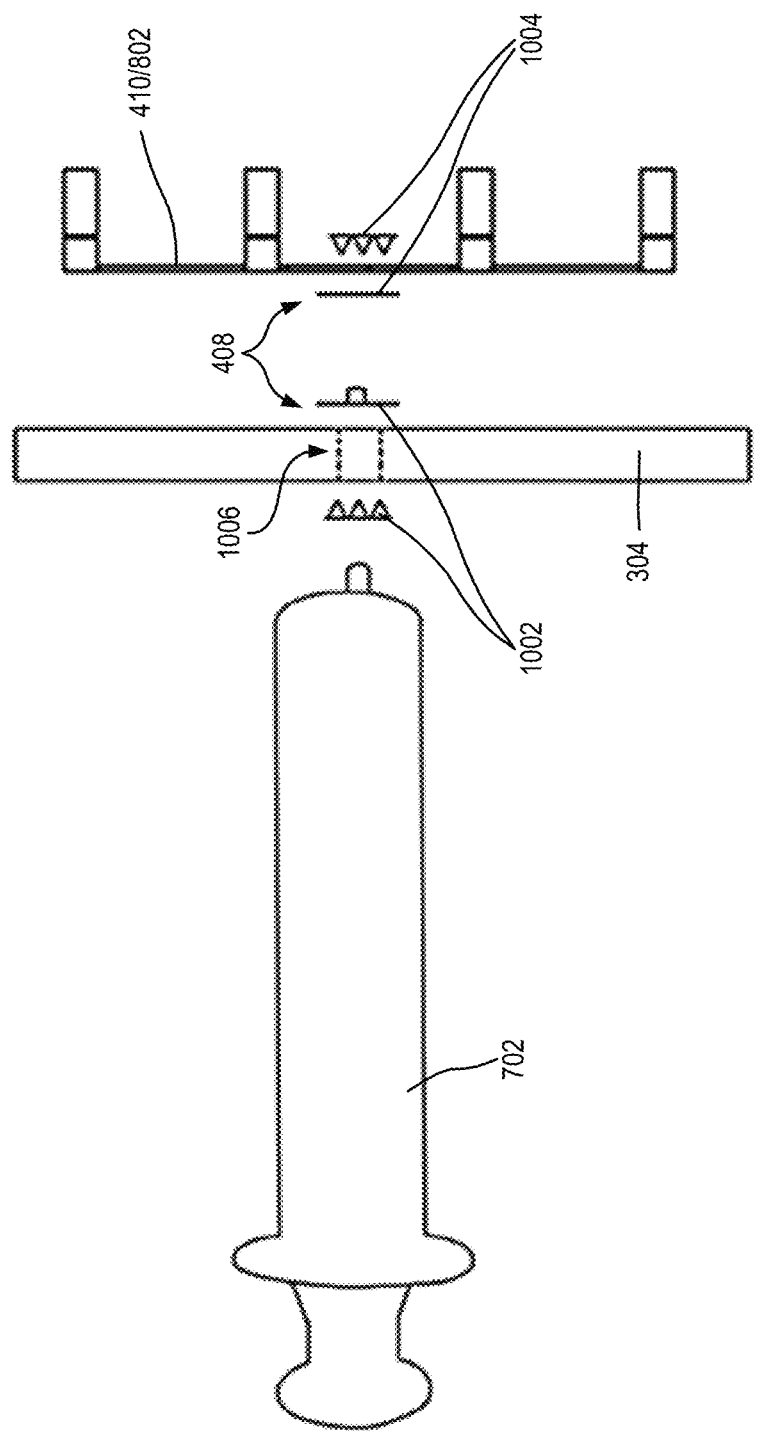
FIG. 10 shows a cross-section of the gel syringe, the chassis/panels, and the snap connector electrode of FIG. 8.
Figure 12A:
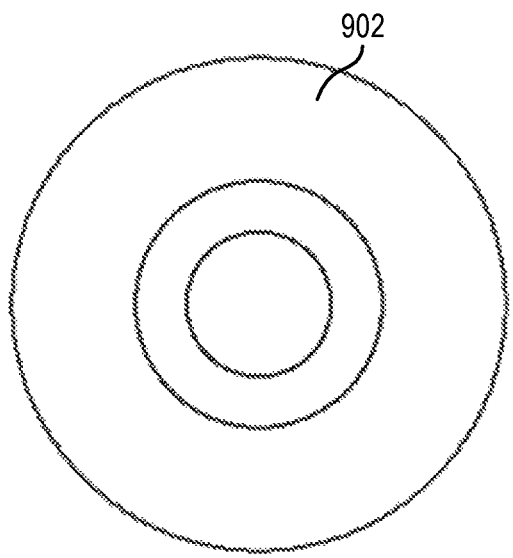
FIGS. 12A-12D show top, side, bottom, and perspective views, respectively, of the cup-style ECG electrode of FIG. 9, in embodiments.
Figure 12B:
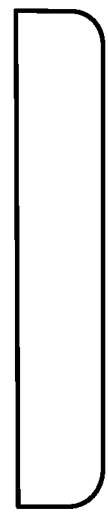
Figure 12C:
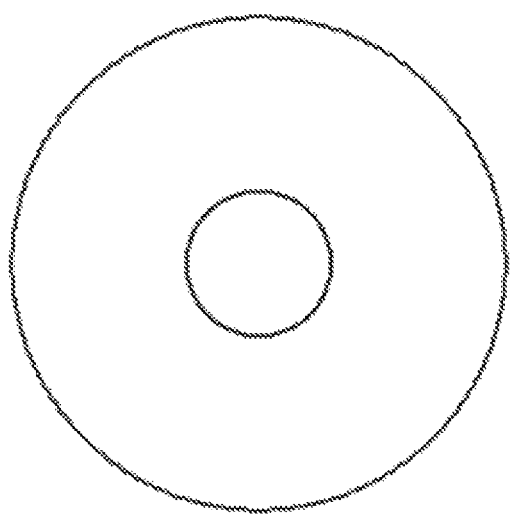
Figure 12D:
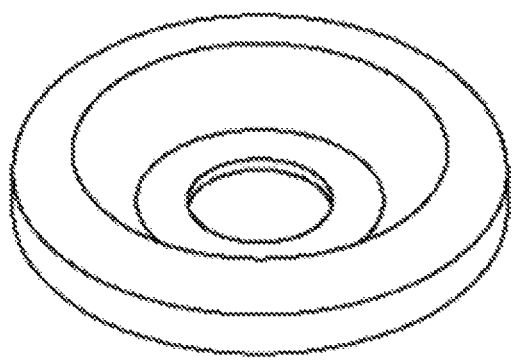

Flexible panels 402 and 404 provide electrical connectivity between an electronics module 406 and one or more of temperature sensors 208, ECG sensors 210, and auscultation sensors 212. Accelerometer/motion sensors 214 and ambient temperature and humidity sensors 216 may be included within electronics module 406. As shown in FIG. 10, to electrically (and physically) couple flexible panels 402 and 404 with removable ECG electrodes 410(1)-(3), a male side 1002 of snap connector electrode 408 (e.g., a Dritz snap connector) passes through a hole 1006 in a gold plated copper pad of the flexible panel. A female side 1004 of snap connector electrode 408 is attached to removable ECG electrodes 410. Male side 1002 passes through a hole 318 in soft chassis 302, and mates with female side 1004 of the snap on removable ECG electrodes 410. Advantageously, the snap hold flexible panels 402, 404 in place within soft chassis 302, and makes good electrical connection between the gold pad on the flexible panel and the removable ECG electrodes 410. Movement and/or breathing of the animal serves to close this connection, making it unlikely to come undone while worn. Removable ECG electrodes 410(1)-(3) are shown as comb-style electrodes, but could be other styles. As shown in FIG. 4, in certain embodiments, animal harness 102 uses three snap connector electrodes 408(1)-(3) and three removable ECG electrodes 410 to collect ECG data and/or pulse/heart rate of the animal.

Removable ECG electrodes 410 are designed for operation on a very hairy surface (e.g., an animal's coat), possibly without requiring a conductive electrolyte or gel, such as when signal processing is used. This type of removable ECG electrode 410 is very useful if a good ECG signal is desired without shaving fur from the animal. However, removable ECG electrodes 410 may be made from 316 stainless steel and used with one or more of a Hydrogel, Saline, and Alcohol as the conductive electrolyte to improve conductivity between the electrode and the skin of the animal.

Activity:

Accelerometer/motion sensors 214 may include a 3-axis accelerometer that measures one or both of the animal's motion and orientation in space. Motion sensors 214 may be used to monitor activity of the animal, the gait of the animal, and the orientation of the animal. In certain embodiments, accelerometer/motion sensors 214 are configured to indicate (e.g., change the logic on an external pin from high to low) when acceleration on a certain axis exceeds a certain threshold. Animal harness 102 may count these acceleration events while in a very low power state to estimate the relative activity level of the animal (e.g., low activity, active, and very active) based on the number of these events over a ten second period. Similarly, these counts may be stored and averaged to give a more representative estimate of activity over a period (e.g., one minute). In other embodiments, raw acceleration information from all axes of accelerometer/motion sensors 214 may be sampled at high or low rates and transmitted to the server or user for viewing and additional analysis.

Environmental Conditions:

Ambient temperature and humidity sensor 216 may be positioned on an external surface of electronics module 406, where it is protected from damage by a plastic cover and from dirt by a breathable mesh window in soft chassis 302 (e.g., when electronics module 406 is inserted into a pocket 320 of soft chassis 302). This configuration allows protection of ambient temperature and humidity sensor 216 while allowing adequate ambient airflow to the sensor such that it may accurately read the environmental temperature and relative humidity in the immediate vicinity of the animal wearing animal harness 102. Ambient temperature and humidity sensor 216 (e.g., environmental conditions of the animal) may be sampled once every ten seconds and may be sent to mobile device 122 and/or server 104.

Pulse/Heart Rate

Animal harness 102 positions snap connector electrodes 408(1) and 408(3) and corresponding removable ECG electrodes 410(1) and 410(3) on either side of the animal and positions snap connector electrode 408(2) and corresponding removable ECG electrode 410(2) in the center of the animal's back (to reduce signal noise). In one embodiment, electronics module 406 samples ECG sensors 210 at a rate of 150 Hz in a low power mode, for example. Every ten seconds, the ECG signal is processed with filters, thresholds, and differential analysis tools to detect R and S components of the ECG waveform. The Beats Per Minute (BPM) is calculated based on the number of RS waveforms detected in the ten second sample. In one embodiment, the BPM estimate for six, ten second samples are stored and averaged to reduce the effects of random error and provide the user with more representative BPM value for any given minute. However, other averaging periods (e.g., averaging the last three samples) may be used without departing from the scope hereof. Processed BPM measurement and raw ECG signals may be sent to the user or the server for viewing and analysis.

Flexible panels 402 and 404, and electronics module 406, fit inside a cavity 305 of soft chassis 302, and zipper 340 may be closed. Soft chassis 302 protects sensors 208, 210, 212, 214, and 216, flexible panels 402 and 404, and electronics module 406 and holds the sensors 208, 210, 212, 214, and 216 positioned on flexible panels 402 and 404 tightly against the body of the animal (e.g., canine).

Temperature sensors 208 are positioned on offshoots 412 and 414 of flexible panels 402 and 404, respectively, that fit into a cavity formed within lower portions 307 and 308 of axillary straps 306 and 308, respectively. That is, cavity 305 of main body 304 extends into lower portions 307 and 309. Lower portions 307 and 308 may be thermally insulated on the side of the strap facing away from the body of the animal when animal harness 102 is worn. This insulation mitigates the effects of outside environmental conditions on the readings of temperature sensors 208 and allows for accurate estimations of animal body temperature. In one embodiment, animal harness 102 includes eight temperature sensors 208, four positioned on each offshoot 412 and 414, to measure animal temperature from the axillary region of the animal. These eight temperature sensors 208 allows a temperature profile of the axillary region of the animal to be measured for both sides of the animal to provide better estimates of body temperature for animals of different body types and sizes.

Temperature data may be sensed every ten seconds, temperature data is captured from all eight temperatures. Electronics module 406 may determine a maximum value of the eight temperature sensors may be stored as the Max Body Temperature (MBT). Animal harness 102 may keep track of the last six MBT measurements (e.g., taken every ten seconds over 60 seconds) and an average of these MBT values, and all individual sensor values, may be reported to server 104 and/or mobile device 122.

The multiple sensors located along the length of the axillary strap provides redundancy and makes the readings more robust and independent to changes in body type and size of different animals.

In certain embodiments, a radiation shield is formed of a reflective material that is positioned outside temperature sensors 208 to retain animal body heat on the sensor (e.g., instead of the heat radiating away). For example, the insulation at lower portions 307 and 308 may include a metallicized or reflective film. This reflective insulation may also reflect radiative heat from external influences away from temperatures sensors 208.

In certain embodiments, at least lower portions 307 and 308 of animal harness 102 have a black material positioned towards the animal, and a white or reflective material on the outer surface. These colors are selected to provide more accurate body temperature measurements using temperature sensors 208. In certain embodiments, a majority of animal harness 102 may include reflective and/or colored material, that is selected to reduce the effects of radiative heat from the environment from influencing temperature measurements and/or from heating the animal.

Zipper 340 runs down the length of main body 304 that allows the chassis to open and expose cavity 305. Pocket 320 has a circular hole 322 covered in mesh (see mesh 706, FIGS. 7, 8 and 9) is formed in the center of main body 304 on top of soft chassis 302 to receive electronics module 406 when flexible panels 402 and 404 are inserted into cavity 305. Hollow lower portions 307 and 309 of axillary straps 306 and 309 receive offshoots 412 and 414 flexible panels 402 and 404 with temperature sensors 208. One or more snaps 324 at key locations of cavity 305 in soft chassis 302 snap through holes 416 in flexible panels 402 and 404 to retain flexible panels 402 and 404 in place.

In certain embodiments, main body 304 has folding regions 326 and 328 where it may partially fold over on itself, the folding amount being controlled by adjustable length straps 330 and 332, respectfully, that attach at either end of the corresponding folding region 326 and 328. Accordingly, a user may adjust a length of main body 304 (effectively adjusting the circumference of animal harness 102 when clasps 310 and 312 of main body 304 are connected) to accommodate different sized animals.

Axillary straps 306 and 308 may also be adjustable in length, and each has one connector 315 and 317, respectfully, at distal ends that attach to connectors 314 and 316, respectively, on main body 304. Connectors 314 and 315 of axillary strap 306 are reversed as compared to connectors 316 and 317 of axillary strap 308 such that only one axillary strap may be fastened to one of the connectors on main body 304. When animal harness 102 is worn by an animal, the hollow lower portions 307 and 309 of axillary straps 306 and 308 passes through the axillary region (e.g., armpit) of the animal, thereby holding temperature sensors 208 therein against the axillary region of the animal. Axillary straps 306 and 308 then cross the chest and opposite shoulder of the animal and connect to connectors 314 and 316 of main body 304 at the back of the animal. Fastening axillary straps 306 and 308 over the chest and across the opposite shoulder of the animal to the connector at the back allows the straps, and thus temperature sensors 208, to be tightened securely to ensure good heat transfer from the animal to the sensors, without pulling tension or pressure into the shoulder joint of the axillary region, which would restrict motion and cause rubbing.

Two piezoelectric disc elements 418 are located at both left and right ends of flexible panels 402 and 404 (e.g., four altogether) and may function as auscultation sensors 212 and/or operate to emit vibrations and/or sounds. Each piezoelectric disc element 418 may be used to detect small and large vibrations and pressure changes. In certain embodiments, differences in signals from different ones of piezoelectric disc elements 418 may be used to determined relative locations of anatomical structures, movements of the animal, flow, and/or activity of bodily processes. Piezoelectric disc elements 418 may also be used to determine cardiac anomalies in the animal. One or more piezoelectric disc elements 418 may be driven or powered to produce a signal that may be measured on other (or the same) piezoelectric disc elements 418, the attenuation of this signal may be used to determine composition of the body, direction or speed of fluid (e.g., blood) flow, or other items of interest, similarly or identical to ultrasound measurements. One or more of piezoelectric disc elements 418 may be used to sense chest expansion, respiratory rate, and/or heart rate. Flexible panels 402 and 404 are replaceable by the manufacturer or by the user should one of the flexible panels 402 and/or sensors 208, 210, 212, 214, and 216 be damaged or broken. When the pressure on the discs changes, a voltage is generated across the element which is sampled by the onboard Analog to digital Converter (e.g., in signal conditioning circuits 204). To estimate chest expansion, and therefore respiratory rate, the signal from the four sensors are averaged, then filtered through a bandpass filter. The number of times that the resulting signal crosses a threshold is counted and the respiratory rate in terms of Breaths Per Minute, or BrPM is estimated. The piezo elements are sampled at 15 Hz and the signal is analyzed every ten seconds. Results from six processed samples may be stored and averaged to reduce the effects of random error and to provide a more representative estimate of Breaths Per Minute. Processed data and raw signals may be sent to the user or server for viewing and analysis.

Flexible panels 402 and 404 may be removed from soft chassis 302 and soft chassis 302 may be washed and flexible panels 402 and 404 may be carefully cleaned separately. In certain embodiments, flexible panels 402 and 404 comprise one or more flex-circuits (flexible printed circuit) that position sensors 208, 210, 212, 214, and 216 and/or snap connector electrodes 408 relative to the animal and provide electrical coupling between the sensors and/or electrodes and electronics module 406.

Animal harness 102 (including at least soft chassis 302, PCBs, flexible panels 402, 404, and housing of electronics module 406 (see housing 1402 of FIG. 14) are constructed from fire retardant materials. This is advantageous, since animal harness 102 is a high performance wearable electronics device with large capacity and possibly more volatile batteries. That is, the chassis, panels, circuit boards, and plastic components (or any single component) of animal harness 102 are made from fire retardant or fire-resistant materials.

Figure 5:
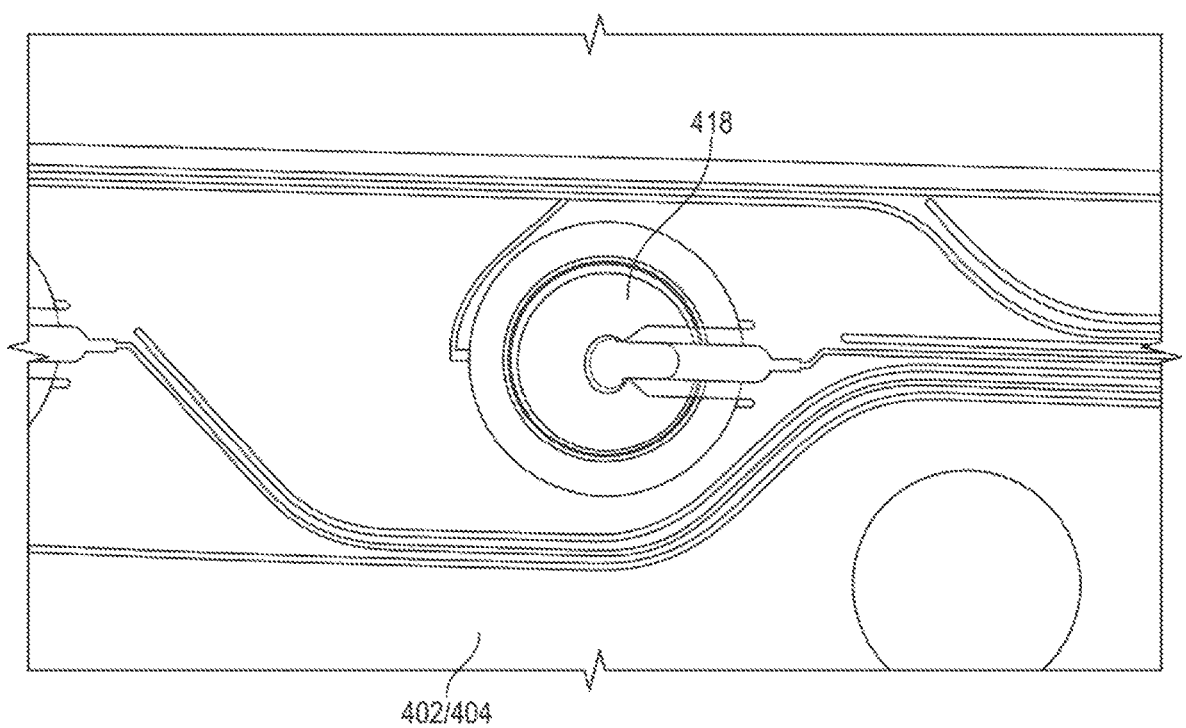
FIG. 5 shows a Piezo element attached to one flexible panel of FIG. 4.

FIG. 5 shows an example piezoelectric disk element 418 electrically and physically connected to one of flexible panels 402, 404 of FIG. 4, such that piezoelectric disk element 418 may measure pressure changes and motion of the chest of an animal configured with animal harness 102. In this example, the back of piezoelectric disc elements 418 is soldered to flexible panel 402, 404, and the top of piezoelectric disc elements is 'lap-soldered' to a 'tab' in flexible panel 402, 404. Advantageously, piezoelectric disk element 418 generates a signal indicative of movement (e.g., flex) in flexible panels 402, 404.

Tension Indicators

Figure 6:
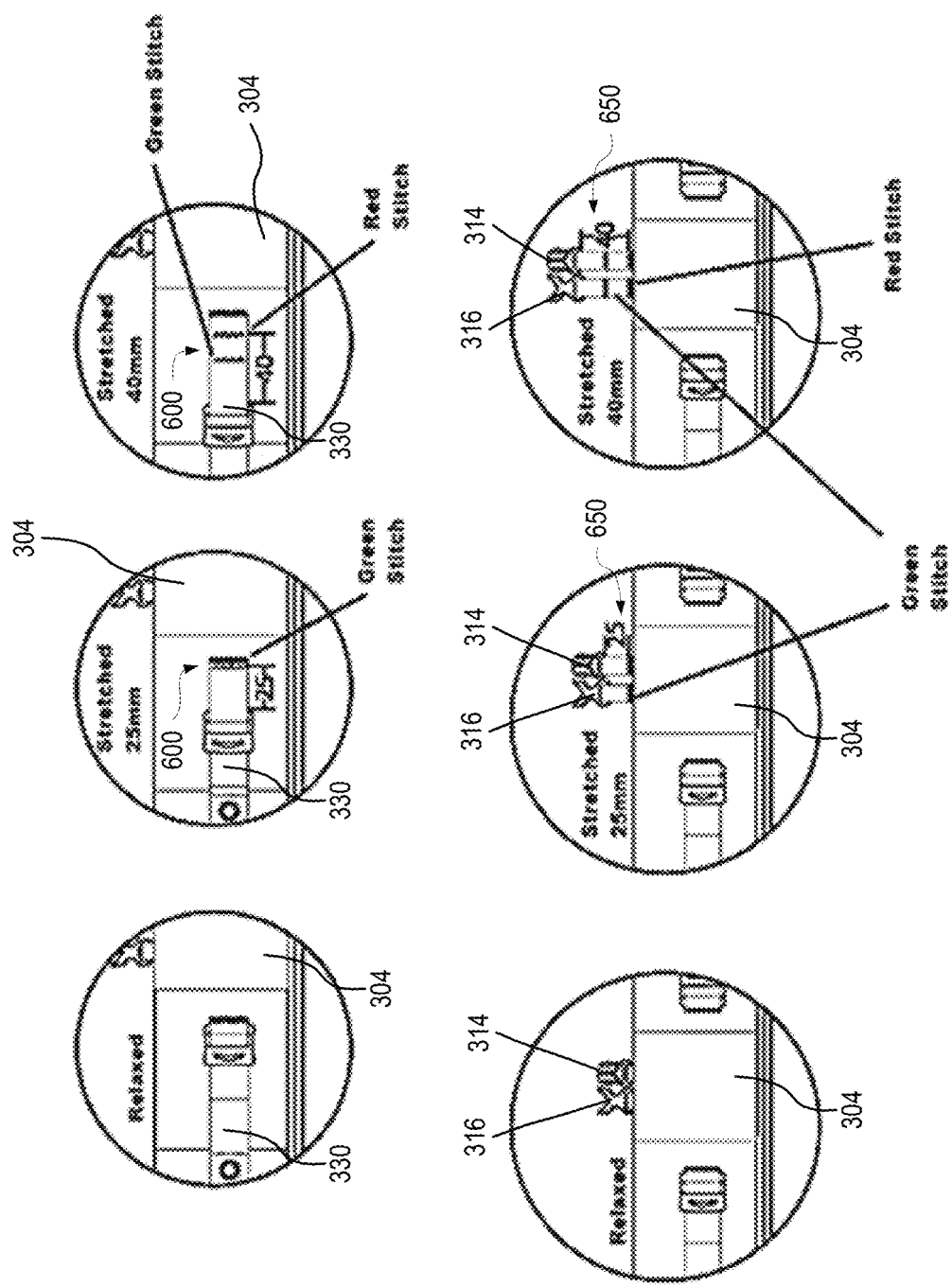
FIG. 6 shows example tension indicators on adjustable length straps and axillary straps of the animal harness of FIG. 1, in embodiments.

FIG. 6 shows first example tension indicator 600 on adjustable length strap 330 and a second example tension indicator 650 on axillary straps 306 and 308, and also showing connectors 314 and 316 of axillary straps 306 and 308. Tensions indicators 600 and 650 are each formed of green stitching and red stitching that provide a visual indication, to a person attaching animal harness 102 to an animal, of when animal harness 102 is adjusted correctly. This facilitates use of animal harness 102 with animals of different sizes and body types. For example, tension indicator 600 ensures correct tension of main body 304 around the torso of the animal and tension indicators 650 ensure correct tension of axillary straps 306 and 308 around the axillary region of the animal. Tension indicators 600 are made from elastic material with colored stitching at different lengths, where the elastic material attaches to adjustable length straps 330 and 332. The elastic is partially covered by a piece of fabric, so that as the elastic stretches with the tightening of adjustable length straps 330 and 332, different colors of stitching are revealed. This ensures that the person attaching animal harness 102 may repeatedly tension main body 304 correctly, irrespectively of the size and body type of the animal. Tension indicators 650 for axillary straps 306 and 308 are constructed similarly, but attach to connectors 314 and 316 located in the middle of main body 304. These locations of tension indicators ensure quick tensioning, and quick visibility of indicators. Chassis may be constructed with or without adjustable straps, or with or without tension indicators, and may include elastic portions designed to provide an acceptable tension range over a range or variety of different animals.

Gel Being Applied to Electrode Through 'Gel-Port'

Figure 7:
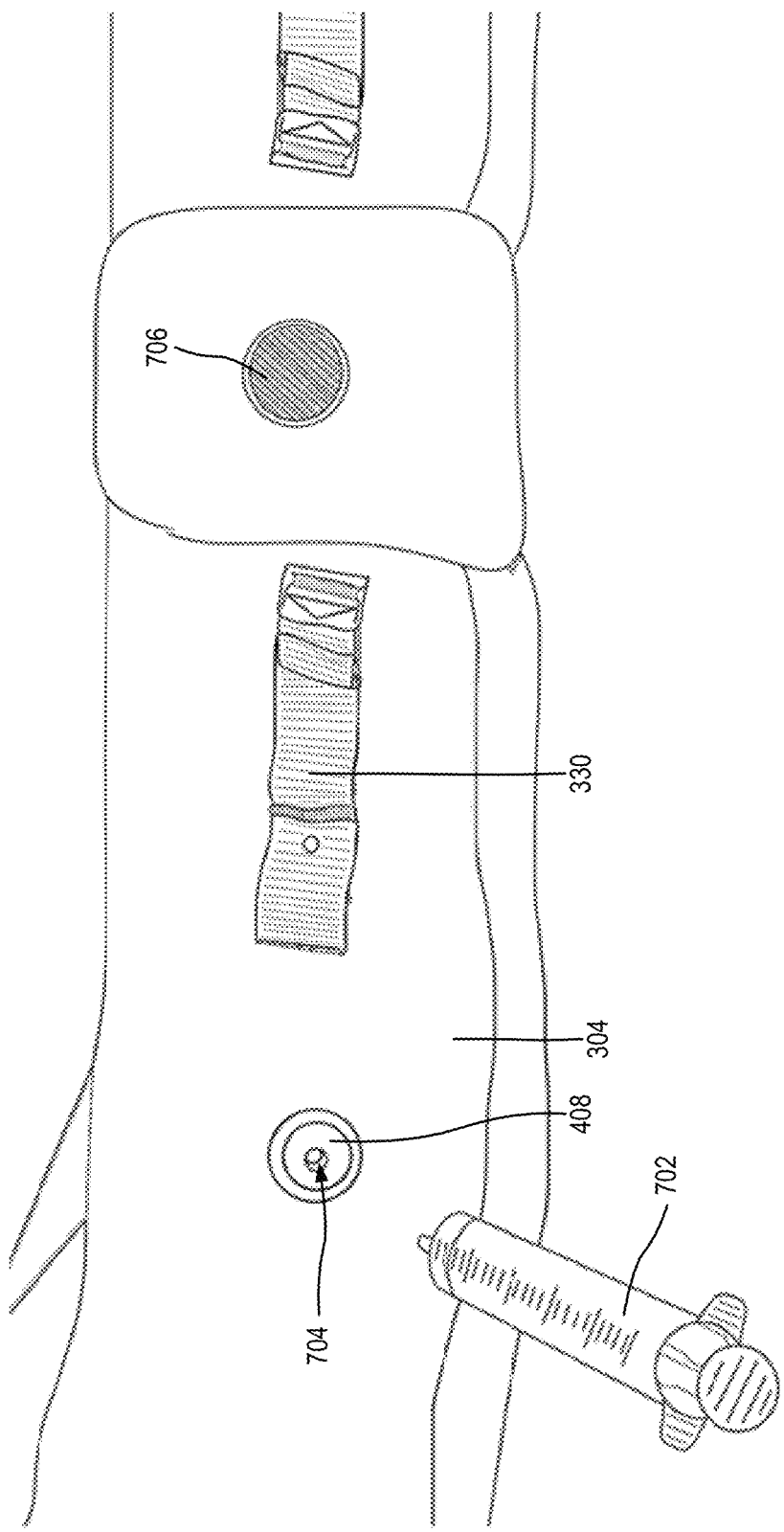
FIG. 7 is a top view of a left side of the animal harness of FIG. 1 with gel being applied through a gel-port of the snap connector electrode, in embodiments.

FIG. 7 is a top view of a left side of animal harness 102 of FIG. 1 with gel being applied through a gel-port of snap connector electrode 408. When animal harness 102 is being worn by an animal, a conductive gel or liquid may be applied directly to snap connector electrodes 408 (e.g., a removable ECG electrode 410) through a gel-port 704 (e.g., a hole) in snap connector electrodes 408. Snap connector electrodes 408 electrically connects with flexible panel 402/404. A standard plastic syringe 702 without a needle, or a squeeze bottle, may be filled with the conductive gel or liquid and applied directly through snap connector electrodes 408 and onto skin underneath, while animal harness 102 is attached to the animal. The conductive gel or liquid increases conductivity between the animal's skin and snap connector electrodes 408, or with other electrodes attached thereto.

Figure 8:
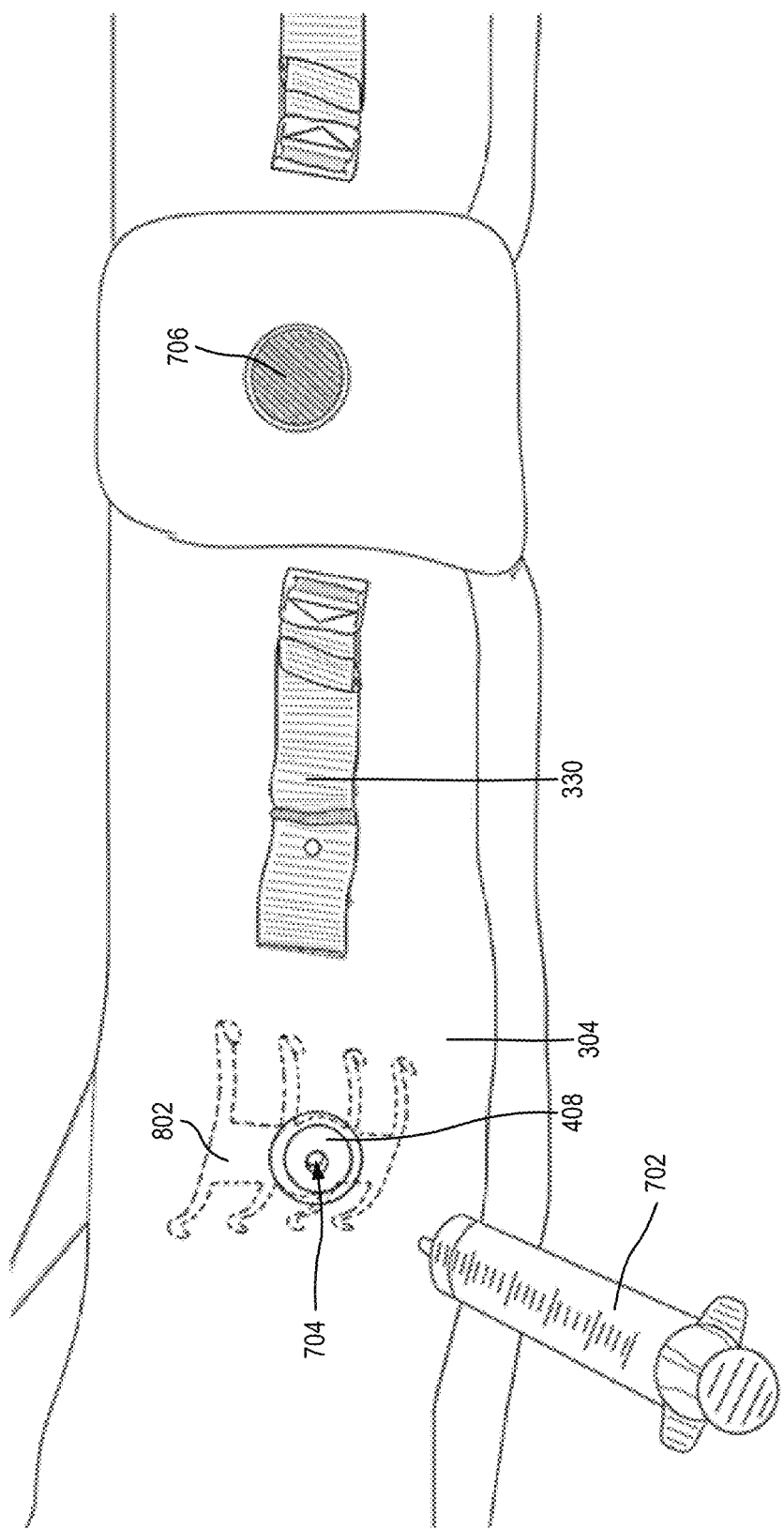
FIG. 8 shows the left side of the animal harness with gel being applied through a 'gel-port' of the snap connector electrode to a comb-style electrode attached on the opposite side of the animal harness, in embodiments.
Figure 9:
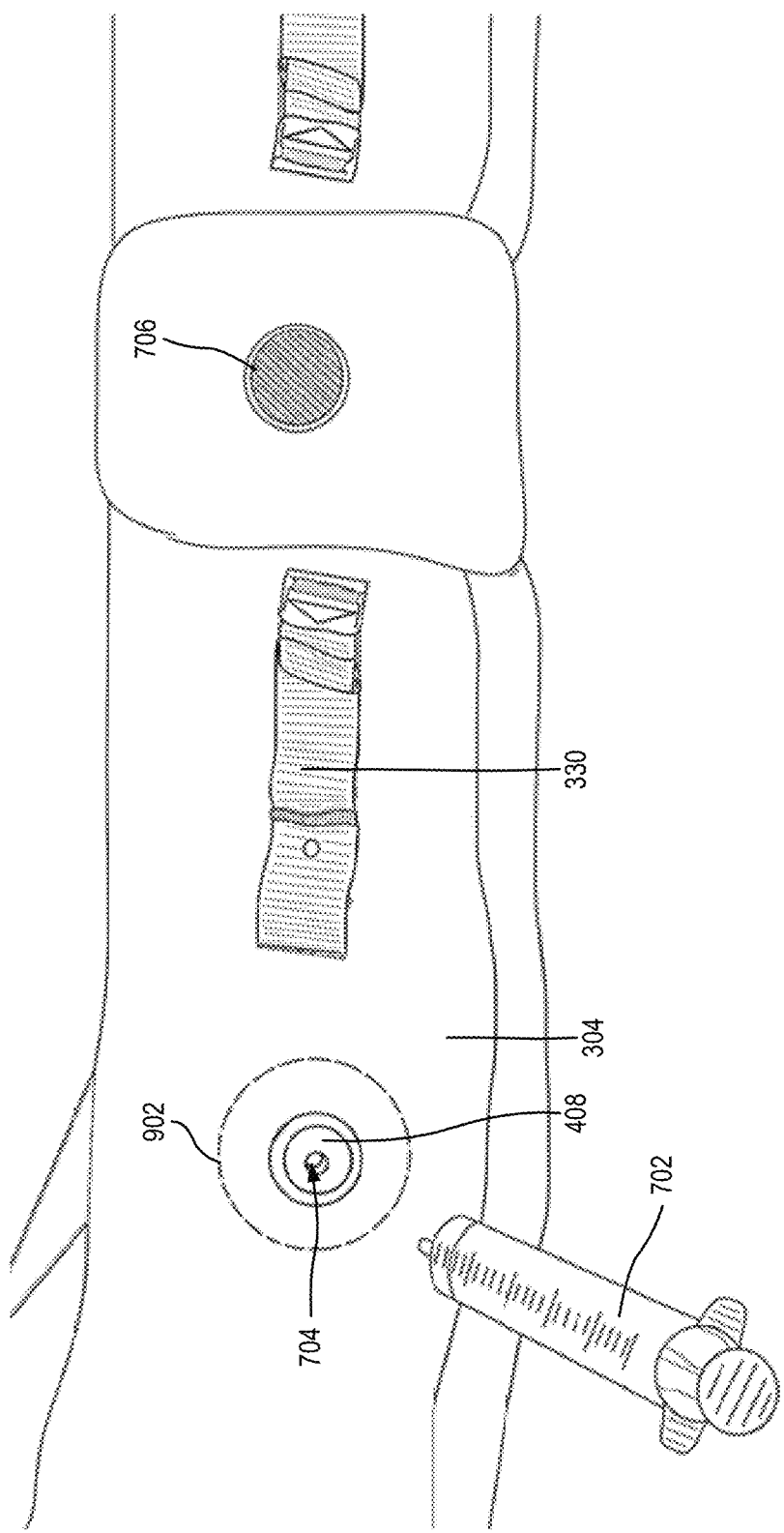
FIG. 9 shows gel being applied through a 'gel-port' of the snap connector electrode to a cup-style electrode attached on the opposite side of the animal harness, in embodiments.

FIG. 8 shows gel being applied to electrode through gel-port 704 of snap connector electrode 408 that has a comb-style ECG electrode 802 (which is an example of removable ECG electrode 410, FIG. 4) attached on an opposite side. FIG. 9 shows gel being applied to electrode through 'gel-port' with cup-style electrode 902 (which is another example of removable ECG electrode 410, FIG. 4) attached on an opposite side. FIG. 10 is a cross-section showing gel syringe 702, soft chassis 302, gel-port 704, and snap connector electrodes 408 coupled with comb-style ECG electrode 802.

Comb-Style Electrode.

FIGS. 11A-11D show top, side, end, and perspective views, respectively, of comb-style ECG electrode 802 of FIGS. 4, 8, and 10. Comb-style ECG electrode 802 may be made from hardened 316 stainless steel (to prevent corrosion and interactions with the skin), cut out by water-jet or stamped out of sheet metal and bent. Prongs are bent back at the tips for animal/patient comfort, and the prongs or legs of the electrode are bent towards the animal to make contact with the skin, and to flex with animal movement, position changes, and external forces. The hole in the middle is for installation of standard dritz snaps, that allow the device to be attached to the chassis/panel assembly. The design is intended to be cheap and easy to mass produce. Materials other than 316 stainless steel may be used including other metals and plastics/polymers.

Cup-Style Electrode

FIGS. 12A-12D show top, side, bottom, and perspective views, respectively, a cup-style ECG electrode 902 designed for use with the conductive gel (e.g., a hydrogel). Cup-style ECG electrode 902 may be used with the animal harness 102 for animals with sensitive skin that does not tolerate comb-style ECG electrode 802. Cup-style ECG electrode 902 may be attached to harness which is then placed on an animal. Once animal harness 102 is on the animal, the conductive gel is applied to the electrode via gel-port 704, the conductive gel works its way through the fur to the animal's skin, and electrical contact is established between the skin and cup-style ECG electrode 902 such that ECG may be measured. Cup-style ECG electrode 902 is design is designed to hold/retain the conductive gel. Cup-style ECG electrode 902 makes less pressure points than comb-style ECG electrode 802, making it more comfortable for the animal. The hole in the center of the cup is for installation of a standard snap (e.g., Dritz), allowing the cup-style ECG electrode 902 to be attached to soft chassis 302 and one of flexible panels 402 and 404. Cup-style ECG electrode 902 may be manufactured from machined 6061 aluminum, but may be made and manufactured from other materials and methods such as metals and plastics, or casting or forming.

An Assembled Animal Harness

Figure 13:
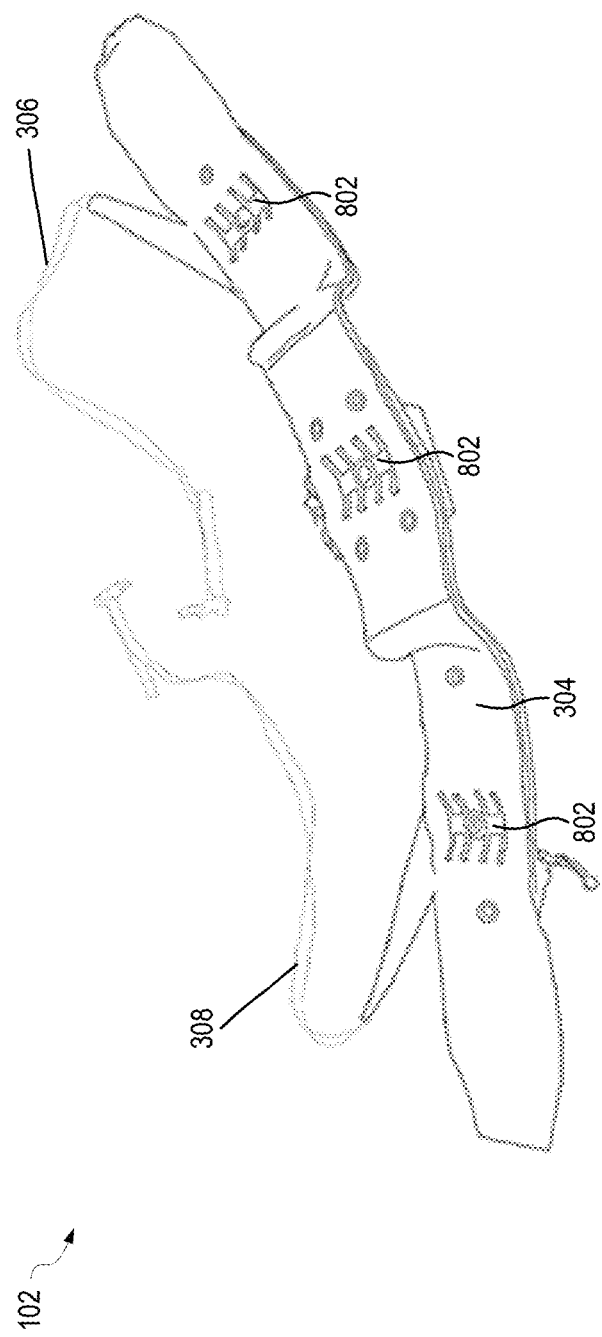
FIG. 13 is a bottom-inside perspective view of the animal harness of FIGS. 1-12 assembled with three comb-style ECG electrodes, in embodiments.

FIG. 13 is a bottom-inside perspective view of animal harness 102 of FIGS. 1-12 assembled with three comb-style ECG electrodes 802. Animal harness 102 is fully assembled and viewed from the bottom, which is the side in contact with the animal's body. Note the location of the three comb-style ECG electrodes 802 configured with main body 304.

Electronics Module Housing and Partial Panel

Figure 14:
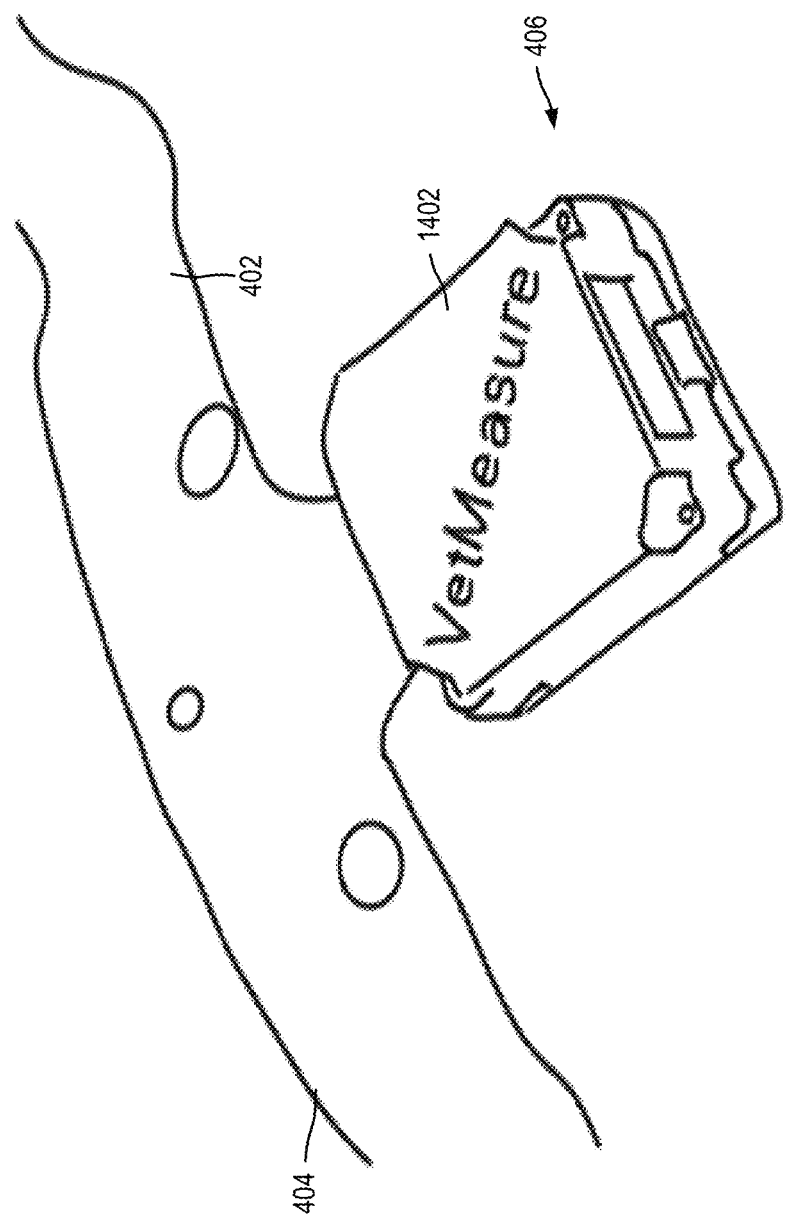
FIG. 14 shows a housing with the electronics module electrically and physically coupled with the flexible panels of FIG. 4, in embodiments.

FIG. 14 shows a housing 1402 with electronics module 406 electrically and physically coupled with flexible panels 402 and 404, a portion of which are shown in FIG. 14. As described above, flexible panels 402 and 404 are flex circuits with tracks that electrically couple sensors 208, 210, 212, 214, and 216 to electronics module 406. Electronics module 406 includes a housing 1402 for protecting electronic components (e.g., microcontroller 202, signal conditioning circuits 204, real-time clock 206, ambient temperature and humidity sensors 216, transceivers 218, onboard storage 220, user interface 222, and power store 224) that form electronics module 406.

Figure 15:
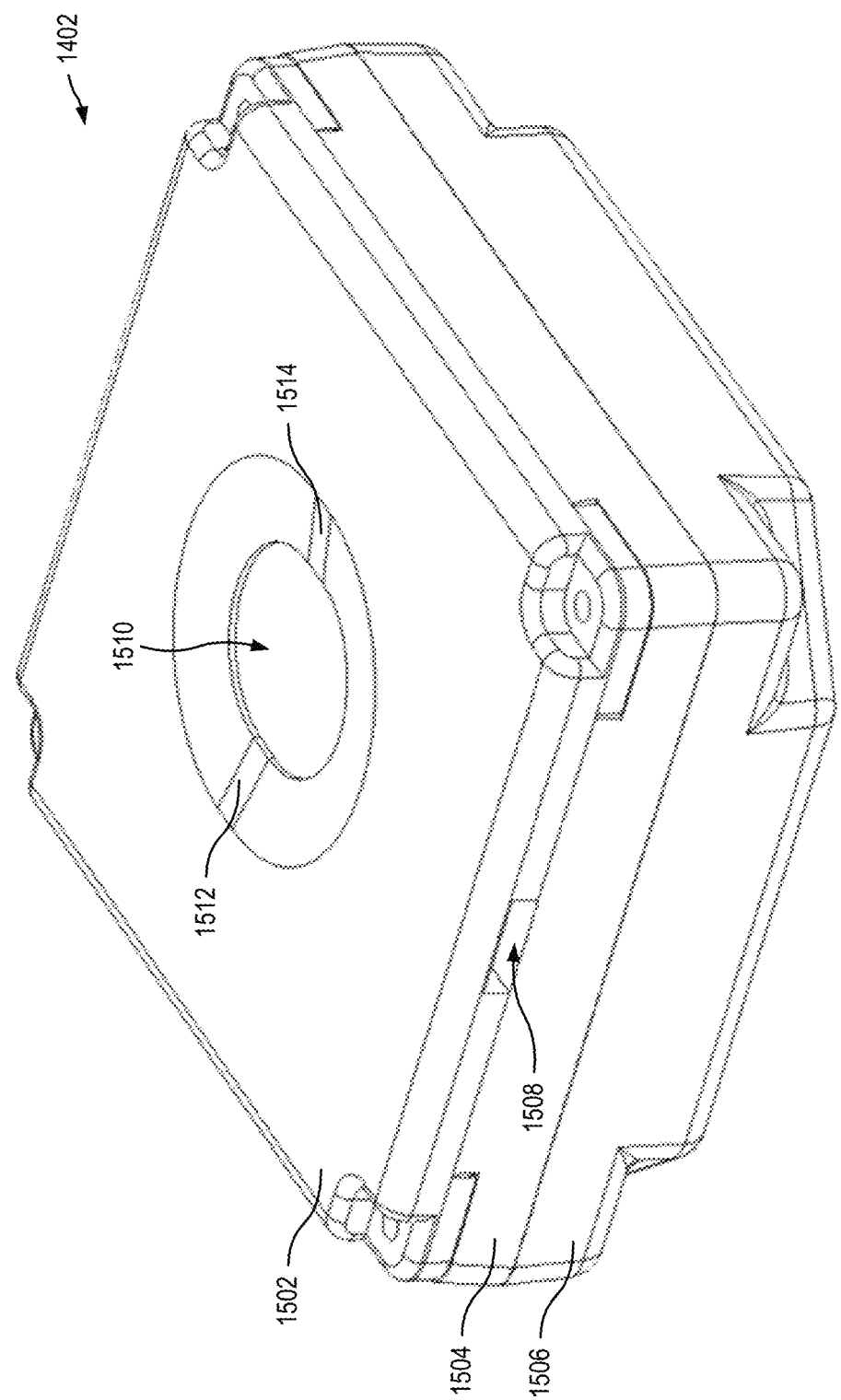
FIG. 15 is a perspective view showing the top side of the housing of FIG. 14, in embodiments.
Figure 16:
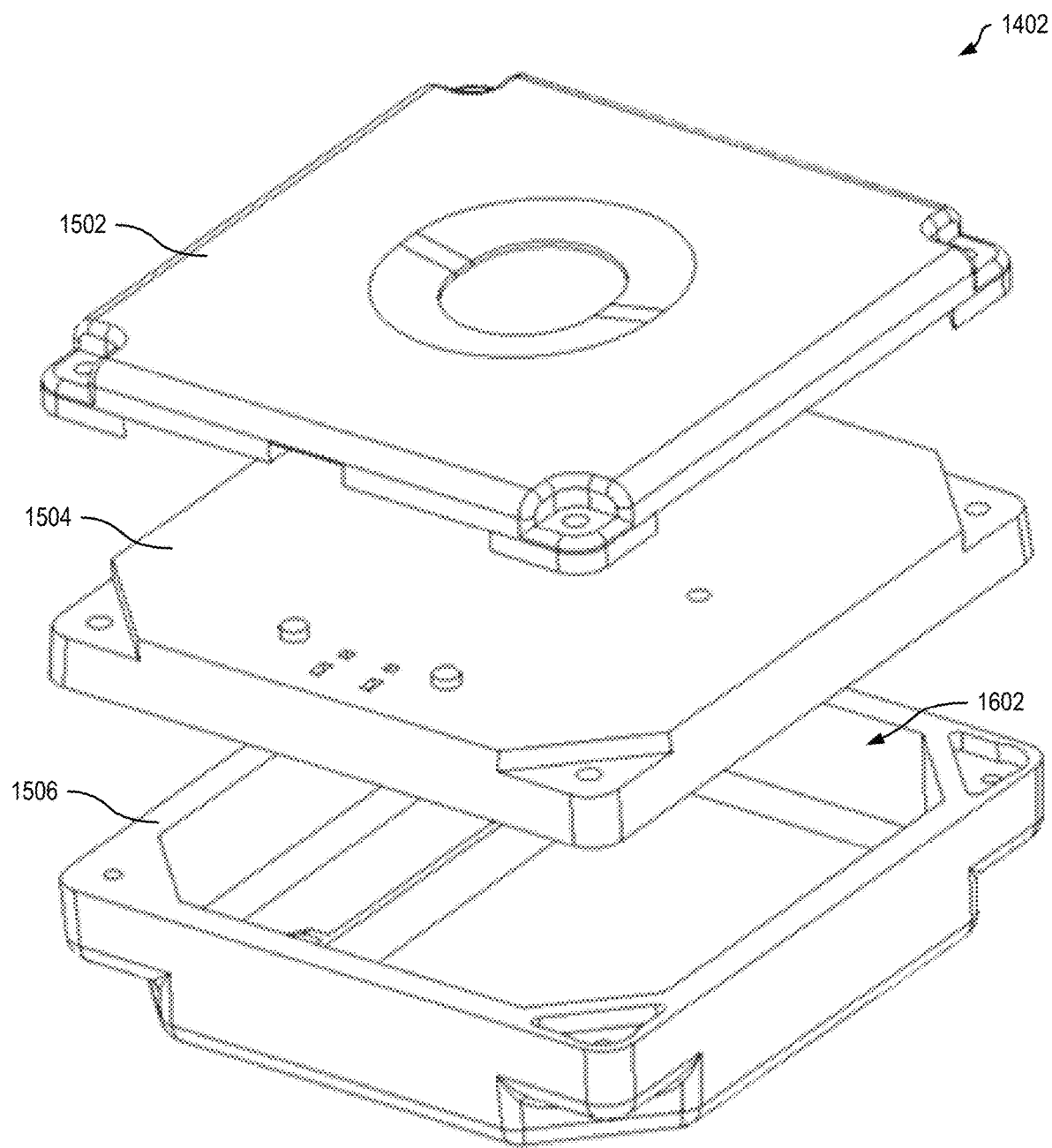
FIG. 16 is an exploded view of the housing of FIGS. 14 and 15, in embodiments.

FIG. 15 is a perspective view showing a top side of housing 1402 of FIG. 14. FIG. 16 is an exploded view of housing 1402. FIGS. 15 and 16 are best viewed together with the following description. Housing 1402 may be formed of a top layer 1502, a middle layer 1504, and a bottom layer 1506 (e.g., fabricated from plastic) that may be held together by screws (not shown) and sealed with a gasket or silicone sealant. In certain embodiments, housing 1402 may include an RF 'reflector' or ground plane (not shown) located at a certain distance (e.g., on an inside surface of bottom layer 1506 or as a layer of a printed circuit board within a lower cavity 1602) from an antenna of transceiver 218 (see FIG. 2) and positioned between an antenna of transceiver 218 and the body of the animal. The RF reflector prevents RF radiation from an antenna of transceiver 218 entering the body of the animal, reflects the RF radiation away from the animal, and improves transmission efficiency and connectivity. A charge port 1508 (e.g., a micro-USB style connector) may be located on housing 1402 for charging power store 224. The charge port may be positioned to prevent access when animal harness 102 being worn by an animal, thereby inhibiting users from charging power store 224 while animal harness 102 is on the animal, as this would be a safety issue.

A touch sensor 1510 and LED(s) 1512, 1514 (e.g., part of user interface 222), environmental temperature and humidity sensors 216, and charge port 1508 are located between top layer 1502 and middle layer 1504, which allows touch sensor 1510 to be touched, the LED(s) 1512/1514 to be seen, and environmental temperature and humidity sensors 216 to be exposed to environmental conditions, while being protected from damage. Power store 224 and most other electronic components are positioned between middle layer 1504 and bottom layer 1506, within cavity 1602.

Waterproofing between flexible panels 402, 404 and housing 1402 of electronics module 406 (e.g., waterproofing of electrical connections between inside and outside of housing 1402) is effective and simple, as compared to other options that are bulky and difficult to manufacture. Flexible panels 402 and 404 exit a seam between middle layer 1504 and bottom layer 1506 of housing 1402 and are sealed using gaskets and/or silicone sealant.

Wear and tear on animal harness 102 may result in a broken sensor. Advantageously, flexible panels 402 and 404 are independently replaceable, thereby allowing only the panel with the broken sensor to be replaced, without requiring replacement of other part of animal harness 102. Particularly, flexible panels 402 and 404 may be replaced by a user, and thus expensive factory or technician servicing is not required. Further, flexible panels 402 and 404 may include a flexible connector service loop (e.g., a strain relief loop) that keeps forces exerted on flexible panels 402 and 404 away from a terminating connector (e.g., within housing 1402). This strain relief loop reduces the likelihood that a connection may open or become broke between flexible panels 402, 404 and a lever operated ZIF connector attached to a rigid printed circuit board (PCB) of electronics module 406. Flexible panels 402 and 404 are reinforced around a hole therethrough, bent backward over themselves, and fixed in place with a screw through the hole, such that flexible panels 402 and 404 are unlikely to be pulled from the connection, and such that the connection is isolated from forces on flexible panels 402 and 404.

Firmware and Algorithms

Figure 17:
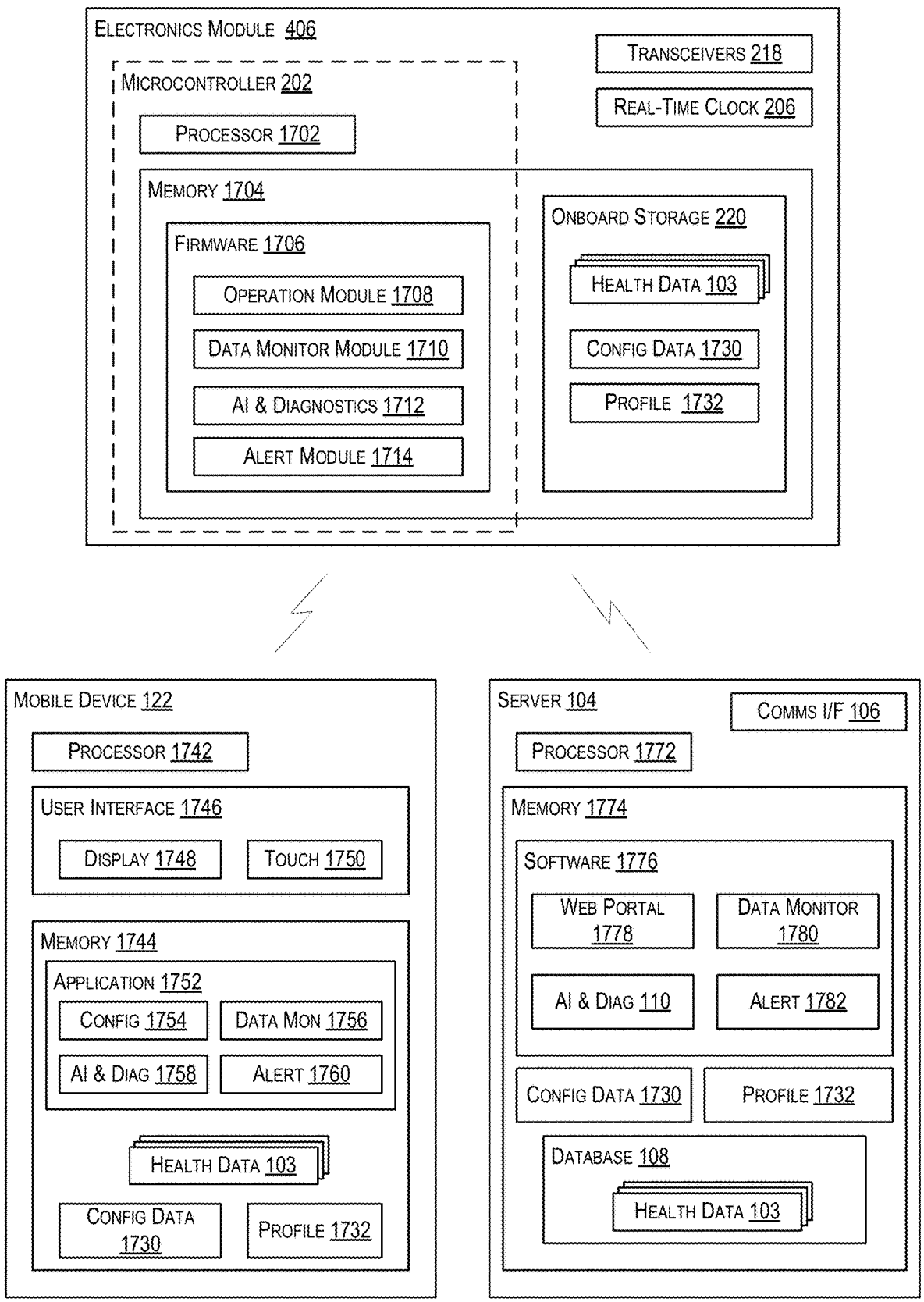
FIG. 17 is a block diagram showing example functionality implemented by the animal health monitoring system of FIG. 1, in embodiments.

FIG. 17 is a block diagram showing example functionality implemented by animal health monitoring system 100, and showing firmware 1706 of electronics module 406, application 1752 (e.g., an App) of mobile device 122, and software 1776 of remote server 104. Electronics module 406 includes microcontroller 202 (see FIG. 2) that may include at least one processor 1702 and memory 1704 storing firmware 1706. Firmware 1706 may include machine readable instructions that, when executed by processor 1702, implement functionality of animal harness 102 as described herein. Mobile device 122 includes at least one processor 1742, a user interface 1746 (with a display 1748 and touch input 1750 for example), and memory 1744 storing application 1752. Application 1752 is for example an app (e.g., iOS, Google, etc.) that is downloaded onto mobile device 122 and includes machine readable instructions that, when executed by processor 1742, implement functionality of mobile device 122 as described herein. Server 104 includes at least on processor 1772 and memory 1774 storing software 1776. Software 1776 may include machine readable instructions that, when executed by processor 1772, implement functionality of server 104 as described herein.

Firmware 1706 may include an operation module 1708 that, based at least in part upon configuration data 1730, controls processor 1702 to, at intervals, read one or more of sensors 208, 210, 212, 214, and 216, determine health status data 103, tag health status data 103 with a current time and date from real-time clock 206, and store the tagged health status data 103 in onboard storage 220. Configuration data 1730 may be set by a user (e.g., via application 1752) to control operation of animal harness 102. Configuration data 1730 may define one or more of an interval for taking measurements from sensors 208, 210, 212, 214, and 216, login credentials for connecting to local gateway 120, and so on.

Electronics module 406 includes transceivers 218 for communicating with other devices and transferring sensed and/or determined health status data 103 (see FIG. 1). Transceivers 218 may implement one or both of Bluetooth and Wi-Fi. Transceivers 218 may implement other wireless protocols (e.g., Ant+, Z-wave, and so on) for communicating with other devices as needed. Animal harness 102 does not require a dedicated hub or base station for receiving sensed or determined data. Rather, health status data 103 is stored in onboard storage 220 of electronics module 406 until a connection with at least one of mobile device 122 and remote server 104 is established. When the connection is established, operation module 1708 may transfer health status data 103 from onboard storage 220 to the connected device. For example, when mobile device 122 establishes a Bluetooth connection with electronic module 406, operational module 1708 may transfer health status data 103 to application 1752 that store health status data 103 in memory 1744. Application 1752 may, in turn, transfer, via one or more of Wi-Fi, cellular, the Internet, etc., health status data 103 to server 104 where software 1776 stores health status data 103 in database 108. In another example, when mobile device 122 establishes a Wi-Fi connection with remote server 104, operational module 1708 may transfer health status data 103 to software 1776 that stores health status data 103 in database 108.

Although shown in memory 1774, database 108 may be implemented in other memory and/or external to server 104. For example, database 108 may be implemented as network attached storage (NAS).

Application 1752 may operate with one or more animal harnesses 102, handling the data independently and allowing the user to view and analyze health status data 103 of multiple animals.

Firmware 1706 may be updated remotely and wirelessly (e.g., over the air) and different firmware may be downloaded to animal harness 102 to allow animal harness 102 to behave and interact in different ways. For example, Firmware 1706 may be updated with a 'Telemetry Mode' function that controls electronics module 406 to stream data at a high rate from one or more of sensors 208, 210, 212, 214, and 216 over Bluetooth and/or Wi-Fi (or another wireless protocol) to mobile device 122 and/or server 104 (or another viewing device) that displays waveforms and/or performs further processing of the streamed data. Accordingly, animal harness 102 may replace much of the existing wired telemetry equipment in a veterinary hospital.

Additionally, or alternatively, firmware 1706 may be updated (e.g., by upgrading and/or downloading replacement firmware) to include functionality that measures a strength of a home Wi-Fi signal (e.g., from local gateway 120) and alerts the user when the signal becomes too weak (e.g., when the animal wearing animal harness 102 has have left the owners home or yard.

Functionality of animal harness 102 may be changed by updating and/or replacing firmware 1706. In certain embodiments, a SDK may be developed that allows third party use of animal harness 102 (e.g., by allowing sensors 208, 210, 212, 214, and 216 to be used in different ways) for different functionality.

Web Interface

Software 1776 of server 104 may include a web portal 1778 that implements one or more of a web site, an API, or other such interface that is accessible via the Internet (WWW) and/or other such networks. Web portal 1778 allows a user to connect to server 104 and view, process, analyze, and/or download health status data 103 and information derived therefrom. For example, web portal 1778 may implement a dashboard type interface where the user may view and manipulate health status data 103, configure animal harness 102, and so on. When animal harness 102 is communicating with server 104 (e.g., connected via Wi-Fi, the Internet, optionally via mobile device 122, etc.), web portal 1778 may allow the user to view live data as it is collected from the animal. For example, web portal 1778 may generate one or more of rolling graphs, max-min displays, and so on. In certain embodiments, the user may, through interaction with web portal 1778, create and/or adjust animal profile 1732 that defines one or more expected ranges of values corresponding to sensors 208, 210, 212, 214, and 216. For example, animal profile 1732 may define a body temperature range with a high limit and a low limit, a pulse/heart rate range with a high limit and a low limit, and so on. Animal profile 1732 may also include animal (e.g., the patient) information such as name, birth date, weight, chest circumference, owner information, medications, and more. The user may set a "safe range" for each health metric measured by animal harness 102, and may configure the manner in which they would like to be alerted (text, email, on-harness visual and audio alerts) should a health metric be determined outside the configured safe range.

In a veterinary practice setting, each user may assign a patient to the "My Patients" tab to receive alerts when the data is no longer within the "safe range". Each user will see all patients in the "All Active" tab, but will only receive alerts for "My Patients." Data for individual animals may be downloaded by certain users.

Software 1776 may also include a data monitor module 1780 that processes health status data 103 as it is received from electronics module 406 against animal profile 1732, and where a measured value is outside the defined range within animal profile 1732, data monitor module 1780 may invoke alert module 1782 to send a notification and/or alert to the user. For example, alert module 1782 may send a notification to application 1752 for output from mobile device 122. For example, the notification may be one or both of visual and audible, such that the attention of the user is attracted. Alert module 1782 may also send one or more of SMS text and/or email (e.g., to mobile device 122), and may, by communicating with electronics module 406, generate one or more visual and audio alerts on the animal harness 102. Accordingly, the user is alerted to the change in condition of the animal wearing animal harness 102.

Mobile Device Interface

Application 1752 may include a data monitor module 1756 that processes health status data 103 as it is received from animal harness 102. When electronics module 406 is communicatively connected with mobile device 122 (e.g., via Bluetooth and/or Wi-Fi), data monitor module 1756 may display health status data 103 as it is received from electronics module 406. For example, data monitor module 1756 may show a rolling ECG graph on display 1748, may show an average temperate value, and so on.

Application 1752 may include a configuration module 1754 that interacts with a user, via user interface 1746, to define configuration data 1730, and then transfer configuration data 1730 to firmware 1706 of electronics module 406 where it is stored in memory 1704 and read by operation module 1708. In certain embodiments, the user may, through interaction with configuration module 1754, create and/or adjust animal profile 1732 that defines one or more expected ranges of values corresponding to sensors 208, 210, 212, 214, and 216. For example, animal profile 1732 may define a body temperature range with a high limit and a low limit, a pulse/heart rate range with a high limit and a low limit, a respiratory rate with a high limit and a low limit, and so on.

In certain embodiments, data monitor module 1756 that processes health status data 103 as it is received from electronics module 406 against animal profile 1732, and where a measured value is outside the defined range within animal profile 1732, data monitor module 1756 may invoke alert module 1760 to generate a notification and/or an alert to notify the user. For example, alert module 1760 may generate control mobile device to generate one or more of a sound, a vibration, and a light.

AI Enhanced Measurement Analysis

Figure 18:
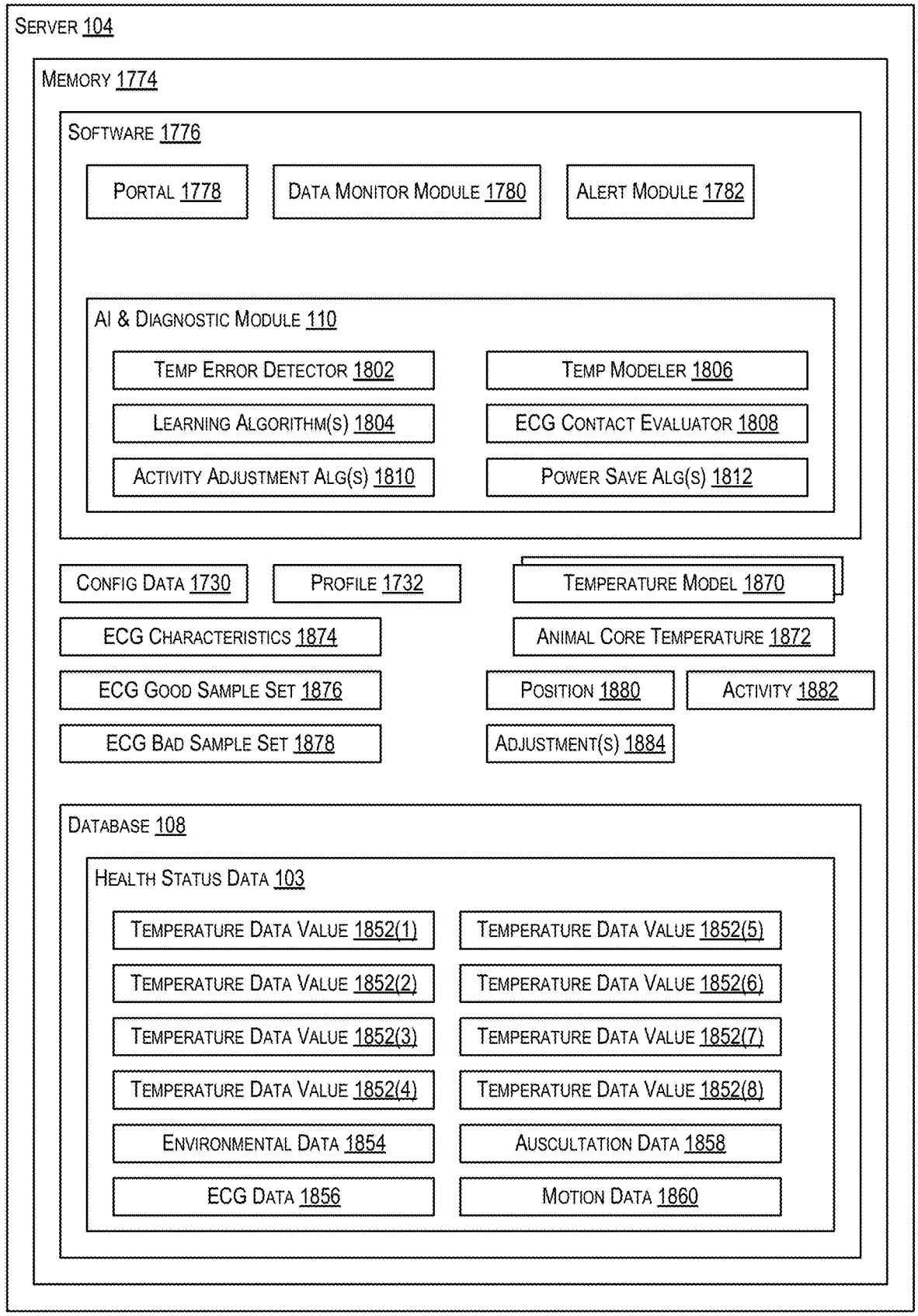
FIG. 18 is a block diagram showing the server of FIG. 1 in further example detail, in embodiments.

FIG. 18 is a block diagram showing server 104 of FIG. 1 in further example detail, and in particular, showing functionality of AI and diagnostic module 110 with associated data. As described above, health status data 103 may be transferred from animal harness 102 to server 104 and stored within database 108. Continuing with the example of FIGS. 4 and FIG. 18, health status data 103 may include four temperature data values 1852(1)-(4) that correspond to the four temperature sensors 208 positioned within axillary strap 306 and four temperature data values 1852(5)-(8) that correspond to the four temperature sensors 208 positioned within axillary strap 308.

As described above, data monitor module 1780 may analyze health status data 103 as it is received in real-time from animal harness 102. For example, data monitor module 1780 may determine an animal core temperature 1872 by averaging temperature data values 1852(1)-(8) corresponding to temperature sensors 208 on axillary straps 306 and 308. However, one aspect of the present embodiments includes the realization that as the animal moves, or the environment changes, certain measurements by animal harness 102 may be affected by these changes and therefore may not be correct. Advantageously, AI and diagnostic module 110 within server 104 may detect when health status data 103 includes temperature measurements that may be incorrect and provide correction and/or notification of such erroneous data.

Although the following description is directed to AI and diagnostic module 110, in certain embodiments, at least part of the described functionality of AI and diagnostic module 110 may also or alternatively be included within one or both of AI and diagnostic module 1758 within mobile device 122 and AI and diagnostic module 1712 within animal harness 102. Similarly, firmware 1706 may implement a data monitor module 1710 that implements at least part of the functionality provided by data monitor module 1780, and may include an alert module 1714 that implements at least part of the functionality of alert module 1782. Although functionality is described in association with particular modules, this for the purposes of illustration only, and other arrangements of computer equipment and firmware may be used without departing from the scope hereof.

In one embodiment, AI and diagnostic module 110 includes a temperature error detector 1802 that detects when temperature change indicated by one or more temperature sensors 208 is non-biological (e.g., not resulting from the animal), and provides an indication to a user that data may be incorrect. For example, temperature sensors 208, positioned within axillary straps 306/308 may occasionally move away from the animal's skin and/or become pressed against different surfaces or exposed to other objects within the animal's environment that results in temperature measurements that are not of the animal (e.g., non-biological). Analysis of previously recorded test data indicates that such occurrences are characterized by a rapid change in measured temperature from one or more (but not all) temperature sensors 208. Since it is impossible, or at least improbable, for a core temperature of the animal to change rapidly, such measurements may be detected as being non-biological temperature changes. Thus, temperature error detector 1802 processes health status data 103 in real-time to detect non-biological temperature changes, and when one or more non-biological temperature changes are detected, temperature error detector 1802 may alert a user (e.g., using a message via application 1752) that animal core temperature 1872 may be erroneous. In certain embodiments, based upon such alerts, application 1752 may instruct the user to take corrective action, such as one of tighten animal harness 102, place a pillow or blanket under the animal if sensors are being pressed to a cold floor, and so on.

In another example, when temperature error detector 1802 determines that a few (e.g., less than the majority) of temperature sensors 208 show non-biological temperature changes, AI and diagnostic module 110 may direct data monitor module 1780 to ignore temperature data values 1852 from these few temperature sensors 208 when generating animal core temperature 1872. Accordingly, animal core temperature 1872 is based on temperature data values 1852 of the other temperature sensors 208 and erroneous values are ignored.

In certain embodiments, AI and diagnostic module 110 may include a temperature modeler 1806 that uses and controls an animal core temperature model 1870 (e.g., implemented within memory 1774) that models animal core temperature based upon a specific animal type, size, breed, and so on. For example, memory 1774 may include many temperature models 1870 and temperature modeler 1806 uses one of these temperature models 1870 based upon characteristics of the animal wearing animal harness 102.

When temperature error detector 1802 detects non-biological temperature changes in one or more temperature data values 1852, temperature error detector 1802 instructs data monitor module 1780 to use temperature model 1870 to generate an estimate of animal core temperature based upon temperature data values 1852. Temperature model 1870 models realistic biological temperature changes and limits changes to animal core temperature 1872 accordingly, and thereby smooths changes in animal core temperature 1872.

In one embodiment, temperature model 1870 provides a maximum temperature change for a given core temperature for the animal using animal harness 102. Accordingly, data monitor module 1780 may limit the change in animal core temperature 1872 to this maximum temperature change. For example, temperature model 1870 may model a maximum rate of temperature change for an animal based upon temperature changes that occur when a similar animal 'spikes a fever' or when a similar animal goes into severe hypothermia. When temperature model 1870 is being used to generate animal core temperature 1872, temperature error detector 1802 may send a notification to warn the user that animal core temperature 1872 is an estimate.

Using temperature model 1870, occasional non-biological temperature readings are effectively filtered out and a reasonable estimate of the animal's core temperature is estimated, at least over a short period. However, when non-biological temperature readings occur for longer periods, the estimated animal core temperature becomes less accurate and the user is instructed to take corrective action.

When temperature error detector 1802 (or data monitor module 1780) determines that one or more temperature data values 1852 exceed a predefined extreme value (e.g., above a maximum value or below a minimum value), irrespective of whether the temperature data value 1852 is determined as non-biological, temperature error detector 1802 alerts the user (e.g., by sending one or more of a notification, a SMS message, and an email) to the extreme temperature value, since it is possible that the animal is being heated or cooled by an external source.

In certain embodiments, AI and diagnostic module 110 may include reliability indicator (e.g., a diagnostic routine) that evaluates agreement of data within health status data 103 to determine a reliability indication of measurements by animal harness 102 and output to the user via application 1752 of mobile device 122. For example, where AI and diagnostic module 110 determines that temperature data values 1852(1)-(8) are in agreement, AI and diagnostic module 110 may determine that reliability of animal core temperature 1872 is high. However, where temperature data values 1852(1)-(8) indicate a broad range of temperature, AI and diagnostic module 110 may determine that reliability of animal core temperature 1872 is low. Accordingly, the user is aware of the reliability of measurements made by animal harness 102, and where reliability is low, the user may adjust animal harness 102 to improve reliability. Further, AI and diagnostic module 110 evaluate health status data 103 over time, wherein the reliability indication is averaged such that intermittent erroneous readings resulting from animal activity for example, may be ignored. The determined reliability indication may also indicate suitability of the animal harness 102 for the animal, and/or may indicate the suitability of one algorithm over another and/or suitability of a processing technique (e.g., filtering etc.).

In certain embodiments, AI and diagnostic module 110 may include at least one learning algorithm 1804 that, at intervals, updates temperature model 1870 to improve accuracy of the modeled temperature. In certain embodiments, learning algorithm 1804 may use other data (e.g., one or more of environmental data 1854, auscultation data 1858, ECG data 1856, and motion data 1860) to further improve temperature model 1870 and thereby determination of animal core temperature 1872. For example, a dog laying down on the floor may be modeled differently from a dog sitting or standing.

In certain embodiments, animal harness 102 may include one or both of pressure and capacitive sensing at temperature sensors 208 to improve estimates of animal core temperature 1872. For example, a force sensitive resistor may be used to measure pressure exerted on the animal's skin by temperature sensor 208. In another example, capacitance between temperature sensor 208 and the animal's skin may be measured to indirectly determine pressure applied by the temperature sensor 208. Further, the measured capacitance may further provide information on effects of the animal's fur on one or more of temperature sensor force, animal fur type, and tension on axillary straps 306 and 308 of animal harness 102.

ECG Contact Evaluation

In certain embodiments, AI and diagnostics module 110 may include an ECG contact evaluator 1808 that determines whether removable ECG electrodes 410 (e.g., comb-style ECG electrodes 802 and/or cup-style ECG electrodes 902) are making good electrical contact, or not, with the animal's body. ECG contact evaluator 1808 receives ECG data 1856 captured by animal harness 102 over a short period (e.g., ten seconds). For example, when animal harness 102 is strapped to the animals and turned on, operation module 1708 may automatically capture and send, for a short period (e.g., ten seconds) animal health data 103 to server 104. ECG contact evaluator 1808 processes ECG data 1856 to extract ECG characteristics 1874 based on ECG features indicative of good and/or bad connectivity of removable ECG electrodes 410. Examples of ECG characteristics 1874 include, but are not limited to, total signal energy, signal energy in a specific region or band of the frequency spectrogram (e.g., above 40 Hz) of the signal, peak values, and so on. ECG contact evaluator 1808 compares ECG characteristics 1874 to each of ECG good sample set 1876 and ECG bad sample set 1878 stored in memory 1774 to determine whether ECG characteristics 1874 indicate that removable ECG electrodes 410 are in good contact with the animal. ECG good sample set 1876 includes sets of characteristics that correspond to ECG data indicated as having good ECG electrode connectivity. ECG bad sample set 1878 includes sets of characteristics that correspond to ECG data indicated as having bad ECG electrode connectivity. In certain embodiments, ECG good sample set 1876 and ECG bad sample sets 1878 may correspond to ECG data 1856 of health status data 103 stored in database 108 and indicated as either good or bad by an operator, or other authorized person, of system 100.

In one example of operation, ECG characteristics 1874 define a coordinate within a multi-dimensional mathematical space and ECG contact evaluator 1808 determines whether ECG electrode connectivity is good or bad by identifying, within the multi-dimensional mathematical space, its 'n' nearest neighbors defined by coordinates corresponding to ECG good sample sets 1876 and ECG bad sample sets 1878, whether those nearest data points correspond to good or bad data sets. ECG contact evaluator 1808 then reports to the user (e.g., using one or more of application 1752, a notification, a text message, and an email) whether removable ECG electrodes 410 are making good electrical connection or whether further adjustment and/or application of a conductive gel or liquid is needed. As noted above, this determination may also be made in one or both of mobile device 122 and/or electronics module 406.

In certain embodiments, one or more of learning algorithm(s) 1804 may be invoked to interact with a person evaluating ECG characteristics 1874, whereby when the person indicates that ECG characteristics 1874 are good, they are added to ECG good sample set 1876 and when the person indicates that ECG characteristics 1874 are bad, they are added to ECG bad sample set 1878, such that system 100 learns, over time, to automatically recognize whether removable ECG electrodes 410 are making good electrical connection with the animal.

Body position and activity of the animal affects accuracy of certain sensors (e.g., one or more of sensors 208, 210, 212, 214, and 216) and measurements made by animal harness 102. To improve accuracy of measurements determined from animal harness 102, AI and diagnostic module 110 includes at least one activity adjustment algorithm 1810 that adjusts processing of health status data 103 based upon detected position and movement of the animal. Activity adjustment algorithm 1810 determines activity 1882 (e.g., running, walking, stationary, and so on) and/or position 1880 (e.g., standing, lying, siting, and so on.) of the animal wearing animal harness 102 based upon health status data 103. Activity adjustment algorithm 1810 may then generate one or more adjustments 1884 (e.g., processing parameters) that adjust processing of certain data based upon position 1880 and activity 1882. For example, where position 1880 indicates that the animal is lying on its back, adjustments 1884 are determined to allow for errant measurements resulting from this position.

Figure 19:
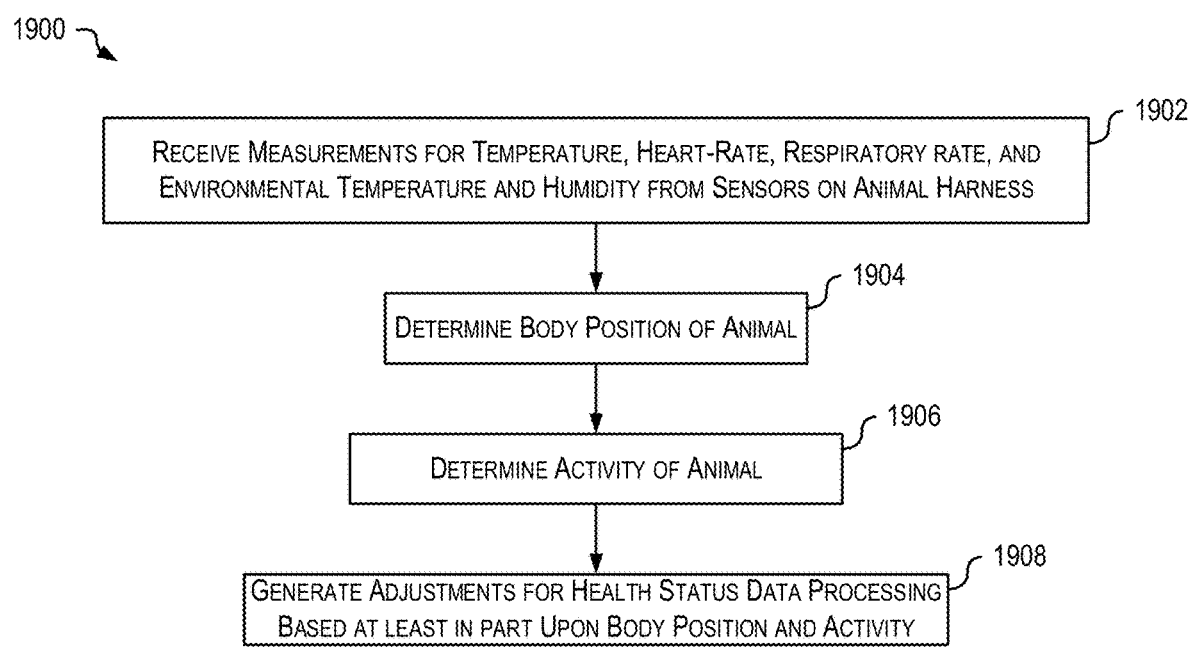
FIG. 19 is a flowchart illustrating one example method for improving accuracy of health metrics determined for an animal wearing animal harness, in embodiments.

FIG. 19 is a flowchart illustrating one example method 1900 for improving accuracy of health metrics determined for an animal wearing animal harness 102. In certain embodiments, method 1900 is implemented in AI and diagnostic module 110 of server 104. However, method 1900 may also, or alternatively, be implemented in electronics module 406 of animal harness 102 and/or application 1752 of mobile device 122.

In block 1902, method 1900 receives health status data of the animal. In one example of block 1902, AI and diagnostic module 110 receives health status data1 103 from animal harness 102. In block 1904, method 1900 determines a body position of the animal from the health status information. In one example of block 1904, activity adjustment algorithms 1810 determines position 1880 of the animal wearing animal harness 102 from health status data 103. In block 1906, method 1900 determines activity of the animal. In one example of block 1906, activity adjustment algorithms 1810 determines activity 1882 of the animal wearing animal harness 102 from health status data 103. In block 1908, method 1900 generates adjustments for health status data processing based, at least in part, upon body position and activity. In one example of block 1908, activity adjustment algorithms 1810 generates adjustments 1884 based at least in part upon position 1880 and activity 1882. Adjustments 1884 are parameters used by data monitor module 1780 when calculating in calculation of one or more of animal body temperature, heart-rate, respiratory rate, and environmental temperature and environmental humidity. For example, contact between one or more sensors 208, 210, 212, 214, and 216 and the animal's skin and/or ECG electrodes 410 and the animal's skin may vary depending on the position and/or activity level of the animal. By determining the current position 1880 and/or activity 1882 of the animal, activity adjustment algorithms 1810 may predict expected contact issues and make adjustments accordingly.

For example, where the animal wearing animal harness 102 is lying on its back, greater filtering of ECG data 1856 may be required since main body 304 of animal harness 102 provides less force to removable ECG electrodes 410 towards the animal's skin (e.g., pressure applied to a back portion of main body 304 results in less tension on a front portion of main body 304. Similarly, certain of temperature data values 1852 may be erroneous where corresponding temperature sensors 208 have reduced pressure from axillary straps 306 and 308 towards the animal's skin. Accordingly, activity adjustment algorithms 1810 may direct temperature modeler 1806 to select a different temperature model 1870 while the animal is lying on its back.

In certain embodiments, AI and diagnostic module 110 may include at least one power save algorithm 1812 that determines when animal harness 102 is not being worn (e.g., when animal harness 102 is not attached to an animal), and adjusts power usage of animal harness 102 accordingly. In one example, power save algorithm 1812 processes temperature data values 1852 received in health status data 103 to determine whether temperature sensors 208 are measuring body heat of an animal. For example, where temperature data values 1852 indicate similar temperature values to an environmental temperature value of environmental data 1854, and these temperature values are not in a possible body temperature range of the animal, power save algorithm 1812 may determine that animal harness 102 is not attached to, or worn by, an animal, and accordingly, power save algorithm 1812 may notify (e.g., via application 1752 of mobile device 122, a SMS text message, an email, and so on) the user that animal harness 102 is operational but not attached to an animal. Further, power save algorithm 1812 may deactivate at least part of animal harness 102 to save power. For example, power save algorithm 1812 may direct animal harness 102 to enter a power save mode, or to shut off completely. In certain embodiments, operation of animal harness 102 is controlled by power save algorithm 1812 based at least in part upon whether power save algorithm 1812 determines that animal harness 102 is being worn by an animal.

Temperature error detector 1802 may also determine whether a heating device (e.g., a warming blanket) is warming the animal and affecting animal core temperature 1872. For example, where an animal wearing animal harness 102 is lying on, and/or covered by, a warming blanket (or other such heating device commonly used by animal care givers and/or veterinary staff to maintain a desired cote temperature in a sick animal), temperature data values 1852 and/or environmental data 1854 measured by animal harness 102 may be artificially elevated. In one example of operation, temperature error detector 1802 compares environmental temperature within environmental data 1854 to a threshold value and where the indicated temperature is above the threshold value, temperature error detector 1802 determines that a warming blanket (or other heating device) is being used. Since ambient temperature and humidity sensors 216 are thermally insulated from the animal's body (e.g., by cavity 1602 of housing 1402 of electronics module 406), since ambient temperature and humidity sensors 216 may indicate an elevated temperature when a warming blanket and/or other heating device is being used. When temperature error detector 1802 determines that a warming blanket (or other heating device) is being used, temperature error detector 1802 may notify the user that animal core temperature 18752 may be artificially elevated. In certain embodiments, when temperature error detector 1802 determines that a warming blanket (or other heating device) is being used, temperature error detector 1802 may direct temperature modeler 1806 to use a different temperature model 1870 to compensate for use of the warming blanket.

Temperature error detector 1802 may also determine whether the animal is lying on a cold surface (e.g., a tile or concrete floor). For example, some dogs lay down on a cool floor with front legs splayed out, resulting in axillary positioned temperature sensors 208 being pressed directly against the cold floor, affecting temperature measurements therefrom. Advantageously, temperature error detector 1802 determines when the animal lays on the cold floor and notifies the user that animal core temperature 1872 may be artificially lowered. This notification may also instruct the user to take a corrective action, such as placing a blanket or pad under the animal (e.g., for the animal's comfort and/or to improve accuracy of temperature measurements).

In one example of operation, temperature error detector 1802 determines when temperature measured by one or more temperature sensors 208 decreases rapidly. For example, where one or more temperature data values 1852 is significantly lower than previously received values, temperature error detector 1802 determines that the animal is laying on a cold surface where the corresponding temperature sensors 208 are contacting that surface. For example, temperature error detector 1802 may detect where a temperature gradient (e.g., temperature rate of change) of one or more temperature sensors 208 exceeds a maximum temperature gradient of the animal's body. Temperature error detector 1802 may then notify the user (e.g., via one or more of application 1752, a notification, a text message, and email, etc.) that animal core temperature 1872 may be adversely affected, that corrective measures may be taken. In certain embodiments, temperature error detector 1802 may also instruct temperature modeler 1806 to select an alternative temperature model 1870 that automatically compensates for the effects of the cold surface on temperature measurements.

Data monitor module 1780 may detect when one or more of sensors 208, 210, 212, 214, and 216 malfunctions (e.g., breaks, becomes disconnected, stops working, etc.) and notify the user accordingly. For example, data monitor module 1780 may detect where data corresponding to one sensor 208, 210, 212, 214, and 216 is inconsistent with other measurements, and/or with previous measurements, or is at a range limit, and so on, and thereby determine that the corresponding sensor has failed. In response to detecting sensor failure, data monitor module 1780 may generate a notification to the user indicating that animal harness 102 needs servicing. In certain embodiments, data monitor module 1780 may also send a report to server 104, where an operator may contact the user to suggest that the corresponding animal harness needs servicing.

Elastic Tensioning

In the embodiments shown in FIGS. 3A-3C, and 6-9, animal harness 102 uses adjustable length straps 330 and 332 and adjustable length axillary straps 306 and 308 that allow a user to adjust animal harness 102 to provide the appropriate tension for correct operation. In an alternative embodiment, adjustable length straps 330 and 332 and axillary straps 306 and 308 include elastic that allow variability in length such that animal harness 102 may be used with a wider range of animal sizes. Particularly, the elastic within animal harness 102 provides the correct tension for consistent operation without requiring specific adjustment by the user when applying the animal harness to the animal. In one example, adjustable length straps 330 and 332 were replace by elastic straps that provide main body 304 with a consistent tension, irrespective of the size of animal within a given size range, movement of the animal, and so on. That is, animal harness 102 may still be made in different sizes to match a particular type, breed, and age range of the animal, but within that size range, animal harness 102 automatically adjusts to provide the appropriate amount of tension to maintain contact between sensors 208, 210, 212, 214, and 216 and the animal's body. This eliminates the possibility of animal harness 102 becoming loose and of the user incorrectly adjusting tension of the animal harness.

Test Mode

AI and diagnostic module 1712 of electronics module 406 may include one or more diagnostic routines that allow factory testing (or technician servicing) of animal harness 102 to ensure correct operation and/or diagnose problems with animal harness 102. In one embodiment, when mobile device 122 connects with electronics module 406 using Bluetooth (normally used for configuring Wi-Fi credentials in electronics module 406), a technician may enter a special code (e.g., within the Wi-Fi username and/or password) that is detected by operation module 1708 and electronics module 406 enters a factory test mode (also known as a technician mode or servicing mode), wherein the technician may invoke one or more diagnostic routines within AI and diagnostics module 1712. For example, these diagnostic routines may provide the technician with an indication of proper assembly of animal harness 102, results of one or more diagnostic tests, and/or readings from the sensors 208, 210, 212, 214, and 216, battery status, such that the technician may verify correct operation of animal harness 102.

Example of Operation:

Animal harness 102 records ECG (using three ECG electrodes 408/140), chest expansion or auscultation (using four piezoelectric disk elements 418 of auscultation sensors 212), 3-axis acceleration (using accelerometer/motion sensors 214), environmental temperature and environmental humidity (e.g., using ambient temperature and humidity sensors 216), and temperature data from eight temperature sensors 208 located in the axillary regions of the animal. An onboard real-time clock 206 allows the device to report the time (e.g., with millisecond accuracy) that a measurement was taken. ECG, acceleration, and piezoelectric signal (for chest expansion measurements) are recorded continuously at industry standard sampling rates (150 Hz for ECG and 15 Hz for piezo elements). Temperature measurements, environmental measurements, clock sampling, and processing of raw ECG, piezo, and acceleration data, occur every ten seconds. For example, every ten seconds, onboard logic (e.g., firmware 1706) may determine whether to report data to server 104 (e.g., via Wi-Fi and/or the Internet) and/or to mobile device 122 (e.g., via Wi-Fi and/or Bluetooth). The user may configure criteria for reporting data. Animal harness 102 may attempt to send data to server 104 if temperature, pulse/heart rate, and/or respiratory rate measurements are outside maximum and minimum values defined within animal profile 1732 by the user, and/or when a rate of change of these values exceeds a maximum value, which is also user configurable. Animal harness 102 may also attempt to send data to server 104 when a certain amount of time has elapsed since the last data was sent. This time interval is also user configurable. Animal harness 102 also periodically sends high resolution raw sensor data to the server. For example, animal harness 102 may sent ten seconds of raw ECG data 1856 (recorded at a sampling frequency of 150 Hz) to the server every five minutes where the data is stored in database 108. Server 104 may process this data on receipt and compares certain characteristics of the raw ECG signal to other ECG signals in the database (that have been categorized by a human or computer based on signal quality) to determine the quality of the ECG signal. Server 104 may alert the user via the web or mobile application 1752 that electrodes may need to be adjusted, or that additional conductive electrolyte or gel may need to be applied. Periodic high-resolution sensor data may also be used to improve or develop new algorithms, detect sensor wear out, or for other purposes.

Interacting directly with the animal harness, such as by touching a touch sensor or button (e.g., touch sensor 1510), may also cause animal harness 102 to attempt to transmit data to mobile device 122 and/or server 104 (e.g., where it may be viewed by the user). The time of this 'touch' event may be recorded on server 104 and used to identify the time of events of interest to the user (e.g., a veterinarian). This may be accompanied by a similar function on mobile device 122 and/or web app or portal of server 104, each of which may allow the user to enter text and/or voice notes.

The user may configure system 100 to send email or text, or other alerts when physiological conditions leave the user configured ranges defined within animal profile 1732.

The user may also configure system 100 to send text or email alerts when animal harness 102 fails to communicate (e.g., check in) at an interval specified by the user.

Animal harness 102 may store the last six processed measurements, captured at ten second intervals, and averages a number of these measurements (e.g., three measurements, though more could be averaged) to reduce the effects of random error and to provide a more representative sample of the animal's physiological conditions at any given time. These averaged measurements are reported to server 104 along with at least part of the raw data that was used to generate the averages.

Every ten seconds, animal harness 102 advertises on Bluetooth Low Energy (BLE) and allows itself to be connected to by a BLE device (e.g., application 1752 running on mobile device 122) for a short period of time (less than a couple seconds). If a device connects to animal harness 102 in this time, the device may receive the most recent processed data (temperatures, pulse/heart rate, respiratory rate, acceleration/activity, and/or timestamp) from animal harness 102 and then animal harness 102 terminates the connection and returns to normal operation that includes low power measurements and higher power processing of captured data at intervals, decision making, and transmission or advertising.

When mobile device 122 connects to animal harness 102 over BLE, the device may also keep the BLE connection active and request that animal harness 102 stream raw data to the device, so that the raw data (e.g., an ECG waveform) may be viewed in real time on the mobile device.

When animal harness 102 determines that data should be sent to one or both of mobile device 122 and/or server 104 (either because physiological conditions or rates of change are outside the acceptable range set by the user, or because the user configurable amount of time has elapsed since the last data was sent), but animal harness 102 cannot successfully transmit data to either of the mobile device 122 or server 104 (e.g., because Wi-Fi and Bluetooth connection are unavailable), animal harness 102 stores the data in onboard storage 220 (e.g., a non-volatile memory device, such as a FLASH memory chip) and attempts to send the data to one or both of mobile device 122 and/or server 104 when a connection becomes available.

When animal harness 102 cannot send data or notifications/alerts to either server 104 or mobile device 122, and determines, based on user configurable parameters that the animal or wearer may be in danger or have unsafe physiological conditions, and if the user has enabled 'local' alerts, alert module 1714 may flash lights (e.g., LED(s) 1512, 1514) and trigger an audio alarm built into the device to alert those within proximity that the animal may be in danger or unhealthy.

Diagnosis/Big Data/Machine Learning/AI:

During operation of system 100 over time, health status data 103 of many different animal (e.g., different types, breeds, sizes, conditions, etc.) is sent to server 104 and stored in database 108. Data in database 108 may include ECG, chest expansion (auscultation), acceleration/movement, animal core temperature, environmental conditions, animal breed, size, weight, and any medication the animal may be on. A user may interact with web portal 1778 of server 104 to retrieve for further analysis and/or view data for an individual animal. The collected data may be analyzed by humans and/or by artificial intelligence to develop new methods and/or algorithms to help diagnose and/or predict health problems in other animals.

Thus, data from many animals may be used to improve one or more of software 1776, application 1752, and firmware 1706 in system 100. For example, new methods may be added to system 100 to help diagnose and predict health problems in individual animals currently being monitored using animal harness 102. Data in database 108 may be used to understand the efficacy of drugs and treatments and to understand the effects of different factors on health of animals.

Optional Accessories

As shown in FIG. 1, system 100 may include one or more optional accessory sensors 126 that operate as stand-alone devices that communicate with animal harness 102. Each optional accessory sensor 126 may include a transceiver (similar to transceiver 218) and a microcontroller (similar to microcontroller 202) with firmware that communicates with transceiver 218 in electronic module 406 of animal harness 102. Example optional accessory sensors 126 includes a thermometer, a blood pressure monitor, a blood oxygen sensor, a heart-rate monitor, and an activity/acceleration monitor. In certain embodiments, operational module 1708 may include data from one or more optional accessory sensors 126 within health status data 103, such that data from the one or more optional accessory sensors 126 may be displayed, collectively or independently of data collected by sensors of animal harness 102, through one or both of server 104 and mobile device 122. For example, server 104 may generate report(s) on an animal containing processed and raw data captured by animal harness 102 and/or optional accessory sensors 126. In certain embodiments, one or more optional accessory sensors 126 may be used to calibrate one or more sensors 208, 210, 212, 214, and 216 of animal harness 102. System 100 may implement record keeping and practice management onto one or more of application 1752 of mobile device 122 and software 1776 of server 104. Advantageously, system 100 may replace every piece of hardware and software in a veterinary clinic or hospital.

In one embodiment, application 1752 includes a button that allows the user to record one or more of voice notes, voice-to-text notes, and text notes, in associated with health status data 103 captured by animal harness 102. That is, the collected voice note, voice-to-text note, and text note is timestamped and associated with one or both of the user and the animal being monitored by animal harness 102. For example, the voice note, voice-to-text note, and/or text note may be transferred to server 104 and stored within database 108.

Firmware 1706 of animal harness 102 captures data continually (e.g., at various sample rates, as described above), processes that data, at intervals, and transfers that data to one or both of mobile device 122 and/or server 104. Application 1752 also allows the user to stream raw data captured by animal harness 102 directly to mobile device 122, where application 1752 may display that data to the user in real-time. For example, where the user, interacting with application 1752, request display of live data from animal harness 102 and/or optional accessory sensors 126, application 1752 controls mobile device 122 to connect with animal harness 102, and within ten seconds, displays high resolution sensor data streamed from animal harness 102.

Application 1752 may also control a camera of mobile device 122 to capture, under control of the user, one or more images of the animal (e.g., showing symptoms, a procedure on the animal, a recovery phase, and so on) that are time stamped and stored in association with the animal being monitored by animal harness 102 and/or the user. For example, the photographs may be transferred to server 104 and stored within database 108.

Application 1752 and/or web portal 1778 may include additional fields that allow the user to enter other medical data that may be recorded, timestamped, and stored in association with the animal and/or the user. For example, these fields may correspond to data recorded on a regular anesthesia sheet used in surgeries. Accordingly, system 100 may record other medical information and store it in association with the animal and/or the user. That is, the user (e.g., a veterinarian) may use system 100 to replace one or more existing methods used in a clinic or practice to record the medical information. In certain embodiments, system 100 may integrate and/or cooperate with other existing medical data systems. For example, system 100 may also collect and store data on one or more of medical procedure, laboratory work (e.g., blood/sample test results), drugs and medications used and prescribed, observations (e.g., on one or more of: Appearance, Integumentary, Musculoskeletal, Respiratory, Digestive, Genitourinary, Ears, Neural systems, Lymph nodes, Eyes, Circulatory, Mucous membranes), Preanesthetic (e.g., doses, amount given, route, time), Induction (e.g., doses, amount given, route, time), Intubation tube size, Catheter size/gauge, Name/brand of other systems used for monitoring, Inhalant anesthetics, Fluids (e.g., total amount, type), start and stop times of anesthetics and procedures, Pain scale, and so on. System 100 may also include configurable data fields that may be used for other measurements that may not be automatically filled in by system 100. This data may be stored within database 108.

Software 1776, via web portal 1778 for example, may generate standardized reports from data within database 108.

In certain embodiments, application 1752 may provide at least two different interfaces: one for a veterinary clinic/practice use, and one for an owner of the animal. For example, application may require a user to have a login/password (or other authorization method) to access an account stored by system 100. Accordingly, application 1752 may be used by both veterinary staff and an animal owner, whereby the account accessed through application 1752 defines the interface used.

In certain embodiments, electronics module 406 may include a location device (e.g., one or more of a global positioning system, signal triangulation, and so on) that may be activated, at intervals, to determine a current location of animal harness 102 (and thereby the animal). Operation module 1708 may also read acceleration values from one or more axes of accelerometer/motion sensor 214 and determine whether specific activities are being performed by the animal. In one example, the collected accelerometer data may be processed (e.g., by at least one of application 1752 and software 1776), at intervals, to determine gait analysis of the animal and, over time, identify changes in the gait of the animal.

In certain embodiments, one or both of application 1752 and web portal 1778 may collect and store (e.g., within database 108) food and eating information of the animal, and wherein through the acceleration values, collected by operation module 1708 from one or more axes of accelerometer/motion sensor 214, one or both of application 1752 and software 1776 determines animal calorie burn, which may also be stored, in association with the animal, within database 108.

IoT and Security

A person may keep a dog as a pet so that their home is occupied while the person is away (e.g., at work/school/etc.). The dog has a heightened sense of hearing, as compared to the person, and may sense activity of certain events at, or near, the home before any person would. A barking dog may inform the person of the event when the human is at home, and may deter unwanted home intrusion. However, the dog is unable to notify the human of the event when the person is away, and cannot inform the person when the person returns home. Thus, the person may remain unaware of an intruder snooping around the home while they were away. Advantageously, an animal harness may capture health status data of an animal that may be processed to determine when the animal is witnessing an event, such as home intrusion.

Figure 20:
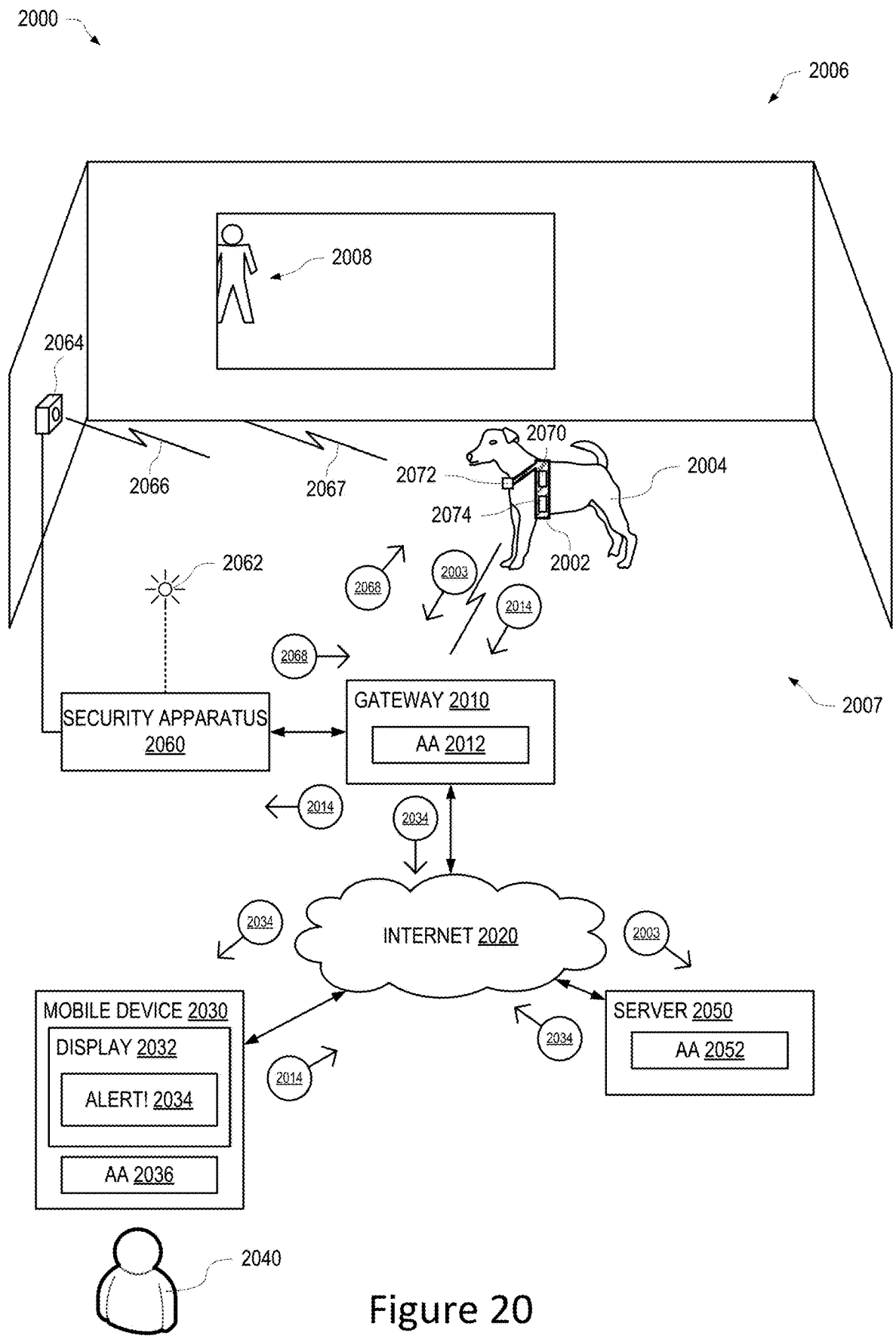
FIG. 20 shows one example system that includes a wireless animal harness attached to an animal (e.g., a dog) that communicates with an Internet gateway (e.g., a home hub, Wi-Fi router, etc.) to improve security and awareness at a location, in embodiments.

FIG. 20 shows one example system 2000 that includes a wireless animal harness 2002 attached to an animal 2004 (e.g., a dog) that communicates with an Internet gateway 2010 (e.g., a home hub, Wi-Fi router, etc.) to provide and/or improve security and awareness at a location 2006. Animal harness 2002 is similar to animal harness 102 of FIG. 1, but is further enhanced to function as an Internet-of-Things (IoT) device by wirelessly connecting with gateway 2010 to extend functionality of animal harness 2002. Animal harness 2002 captures, continuously or at intervals, health status data 2003 of animal 2004 and to send health status data 2003 to gateway 2010. Animal harness 2002 includes a plurality of sensors 2070 including one or more of temperature sensors, ECG sensors, auscultation sensors, accelerometer/motion sensors, and ambient temperature, humidity sensors, and a microphone. In certain embodiments, animal harness 2002 also includes a camera 2072 that may capture video and/or still images and/or audio.

In one embodiment, gateway 2010 is a computing device that includes a processor and memory storing at least one alarm algorithm 2012 that processes health status data 2003 to detect an event 2008 (e.g., a person intruding, a person trespassing, a person snooping, etc.) at location 2006. Alarm algorithm 2012 may be implemented as an artificial intelligence (AI) algorithm (e.g., a neural net) that learns and adapts to one or both of location 2006 and animal 2004 to improve security and awareness. In other embodiments, alarm algorithm 2012 may be generated by AI or other machine learning technique. However, alarm algorithm 2012 may be implemented by other techniques without departing from the scope hereof In other embodiments where gateway 2010 does not include alarm algorithm 2012, gateway 2010 sends, via the Internet 2020 for example, health status data 2003 to a server 2050 (e.g., a computer remotely located from location 2006 and that includes at least one processor and memory) where an alarm algorithm 2052 processes health status data 2003 to detect event 2008. Alarm algorithms 2012 and 2052 may include similar functionality that detects certain changes in health status data 2003 indicating one or more of excitement, agitation, stress, and/or anxiety as animal 2004 witnesses event 2008. For example, a rapid increase in activity (movement), respiration, and/or heartrate within health status data 2003 may indicate that animal 2004 is experiencing anxiety and may be witnessing event 2008. In another example, where animal 2004 is a dog, health status data 2003 may indicate that animal 2004 is barking, growling, and/or whining, whereby alarm algorithms 2012 and 2052 may process health status data 2003 to determine whether animal 2004 is witnessing a security event (e.g., intruder) or a non-security event (e.g., a reaction to another animal). In another example, alarm algorithms 2012 and 2052 may detect patterns in changes of excitement, agitation, stress, and/or anxiety of animal 2004 indicated by health status data 2003 as animal 2004 witnesses different types of events, including event 2008, whereby alarm algorithms 2012 and 2052 learn characteristics of behavior of animal 2004 to improve interpretation of detected behavior of animal 2004. In embodiments that include camera 2072, when alarm algorithm 2012 detects any of a rapid increase in activity (movement), respiration, and/or heartrate within health status data 2003, alarm algorithm 2012 may automatically trigger camera 2072 to capture one or more of still images, video images, and audio using camera 2072, and send the still images, video, and/or audio to mobile device 2030 for review by user 2040.

A security apparatus 2060 may also be installed at location 2006 and may include conventional types of security sensors 2064 (e.g., glass-break detector, PIR motion sensors, door/window sensor, and so on) that sense intrusion at location 2006. Although security sensor 2064 is shown within internal space 2007, security apparatus 2060 may use one or more security sensors 2064 that are positioned outside internal space 2007. In certain embodiments, when at least one security sensor 2064 of security apparatus 2060 is triggered, security apparatus 2060 may send a message to animal harness 2002, via gateway 2010 for example, to initiate capture of one or more of video, still images, and audio by camera 2072, wherein the video, still images, and/or audio is streamed to mobile device 2030 for display to user 2040. Advantageously, user 2040 may review the video, still images, and/or audio to determine whether animal 2004 triggered security apparatus 2060. In another embodiment, the video, still images, and/or audio may be processed by one or more AI algorithms (e.g., within one of alarm algorithms 2012, 2036, and 2052) that detect human forms in the video and/or still images, and/or detect human sounds in the audio, to determine and/or confirm the cause of the detected event as being an intruder and not animal 2004.

In another embodiment, when security sensor 2064 is triggered, it may transmit a wireless enquiry signal 2066 that may be detected by animal harness 2002 when animal harness 2002 is near to security sensor 2064. Enquiry signal 2066 causes animal harness 2002 to transmit, in response, a coded signal 2067 that may be detected by security sensor 2064. Advantageously, security sensor 2064, and/or security apparatus 2060, may thereby determine that animal harness 2002, and therefore animal 2004, is nearby and may have triggered security sensor 2064. Accordingly, security apparatus 2060 may prevent false alarms caused by animal 2004. In certain embodiments, security sensor 2064 may detect a signal strength of coded signal 2067 to determine proximity of animal harness 2002 (and thus animal 2004) to security sensor 2064 and thereby determine a likelihood that animal 2004 triggered security sensor 2064. In certain embodiments, one or more algorithms (e.g., AI) within one or more of gateway 2010, and/or security apparatus 2060 may use signal strength/reflections of wireless signals (e.g., Wi-Fi, and/or signals 2066 and 2067) to map physical layout of internal space 2007 and thereby determine an accurate location of animal 2004 within internal space 2007.

In certain embodiments, alarm algorithms 2012 and 2052 may implement a behavioral model 2139 and 2159, respectively, for animal 2004 that maps changes in one or more of excitement, agitation, stress, and/or anxiety to events witnessed by animal 2004 at location 2006, such that the behavioral models 2139 and 2159 may be used to evaluate changes in the one or more of excitement, agitation, stress, and/or anxiety determined from health status data 2003 to determine whether the animal is witnessing security event 2008 and/or other events. Further, the behavioral model may be continually updated, based upon health status data 2003 and any confirmed events witnessed by the animal such that performance of alarm algorithms 2012 and 2052 improve over time. That is, through use of the behavioral models 2139 and 2159, alert algorithms 2012 and 2052 learn from experience and past results to improve interpretation of changes in animal 2004 to predict event 2008.

Accordingly, when alarm algorithms 2012 and 2052 determines, from health status data 2003, that changes in one or more of excitement, agitation, stress, and/or anxiety indicate event 2008, gateway 2010 and/or server 2050 sends an alert 2034 (e.g., a notification) to a mobile device 2030 of a user 2040 (e.g., a responsible party, home owner, etc.) of system 2000. Mobile device 2030 may show alert 2034 on a display 2032, and/or may output alert 2034 using other ways, including vibration, sound, spoken words, and so on. Advantageously, user 2040 is alerted to event 2008 and may investigate further.

In certain embodiments, mobile device 2030 includes an alarm algorithm 2036 that includes functionality similar to one or both of alarm algorithms 2012 and 2052. For example, alarm algorithm 2036 may receive health status data 2003 from animal harness 2002 via gateway 2010, via Internet 2020, and/or directly via a short range wireless protocol (e.g., BLE). Alarm algorithm 2036 processes health status data 2003 and when health status data 2003 is indicative of event 2008 at location 2006, mobile device 2030 generates alert 2034 on mobile device 2030 and/or sends an event signal 2014 (e.g., a message) to security apparatus 2060. For example, one or more of gateway 2010, mobile device 2030, and/or server 2050 may send event signal 2014 to security apparatus 2060, such that security apparatus 2060 may trigger an alarm and/or transition to a different alert level (e.g., to use an increased sensitivity for one or more security sensors) when event 2008 is detected by animal harness 2002. In certain embodiments, in response to event signal 2014, security apparatus 2060 may activate one or more lights 2062, internal and/or external, at location 2006, which may act as a deterrent to potential intruders. In certain embodiments, event signal 2014 indicates a level of certainty that event 2008 is detected correctly. Advantageously, security at location 2006 is thereby improved over conventional security systems through use of animal harness 2002 and animal 2004.

In certain embodiments, one or more of alarm algorithms 2012, 2036, and 2052 implements a neural network to distinguish characteristics of health status data 2003 that correspond to real events (e.g., an unknown person intruding, a person trespassing, a person snooping, etc.) of interest to user 2040 (and security of location 2006), as opposed to other events (e.g., a known person visiting, another animal that catches the attention of animal 2004) at location 2006 that are not of interest to user 2040, or do not affect security at location 2006. One or more of alarm algorithms 2012, 2036, and 2052 may implement machine learning such that alarm algorithms 2012, 2036, and/or 2052 improve over time to better discern between important and unimportant events witnessed by animal 2004 at location 2006.

Where no animals are present at a location protected by a security apparatus, one or more motion sensors (e.g., PIR and/or camera) may be installed in an internal space 2007 (e.g., room, passage, etc.) to detect unwanted intrusion. However, where animals (e.g., a pet, dog, cat, etc.) are present and have access to internal space 2007, the animal may inadvertently activate the motion sensor and trigger an alarm of security apparatus 2060. Advantageously, through use of animal harness 2002 with system 2000, gateway 2010, mobile device 2030, and/or server 2050 may discern when security sensor 2064 is triggered by animal 2004 and may activate and/or deactivated security sensor 2064 based on activity and/or location of the animal. For example, alarm algorithms 2012 and/or 2052 may process health status data 2003 to determine whether animal 2004 is active (e.g., moving, roaming, etc.) or inactive (e.g., sleeping, lying down, etc.) and send a corresponding signal to security apparatus 2060. Accordingly, security apparatus 2060 may enable operation of security sensor 2064 when alarm algorithm 2012 and/or alarm algorithm 2052 indicates that animal 2004 is inactive and disable security sensor 2064 when alarm algorithm 2012 and/or alarm algorithm 2052 indicates that animal 2004 is active. Advantageously, security apparatus 2060 activates and deactivates security sensor 2064 automatically based upon activity and/or presence of animal 2004 as determined by one or more of gateway 2010, mobile device 2030, and/or server 2050 based on processing of health status data 2003 captured by animal harness 2002.

In certain embodiments, security sensor 2064 (e.g., a PIR motion sensor or camera based motion sensor), installed in internal space 2007, may be configured to wirelessly detect proximity of animal harness 2002, and thereby proximity of animal 2004, to control activation and deactivation of security sensor 2064. Advantageously, when security apparatus is armed, security sensor 2064 need only be deactivated when animal 2004 is in the same internal space 2007, leaving other motion sensors positioned in other internal spaces active.

Figure 21:
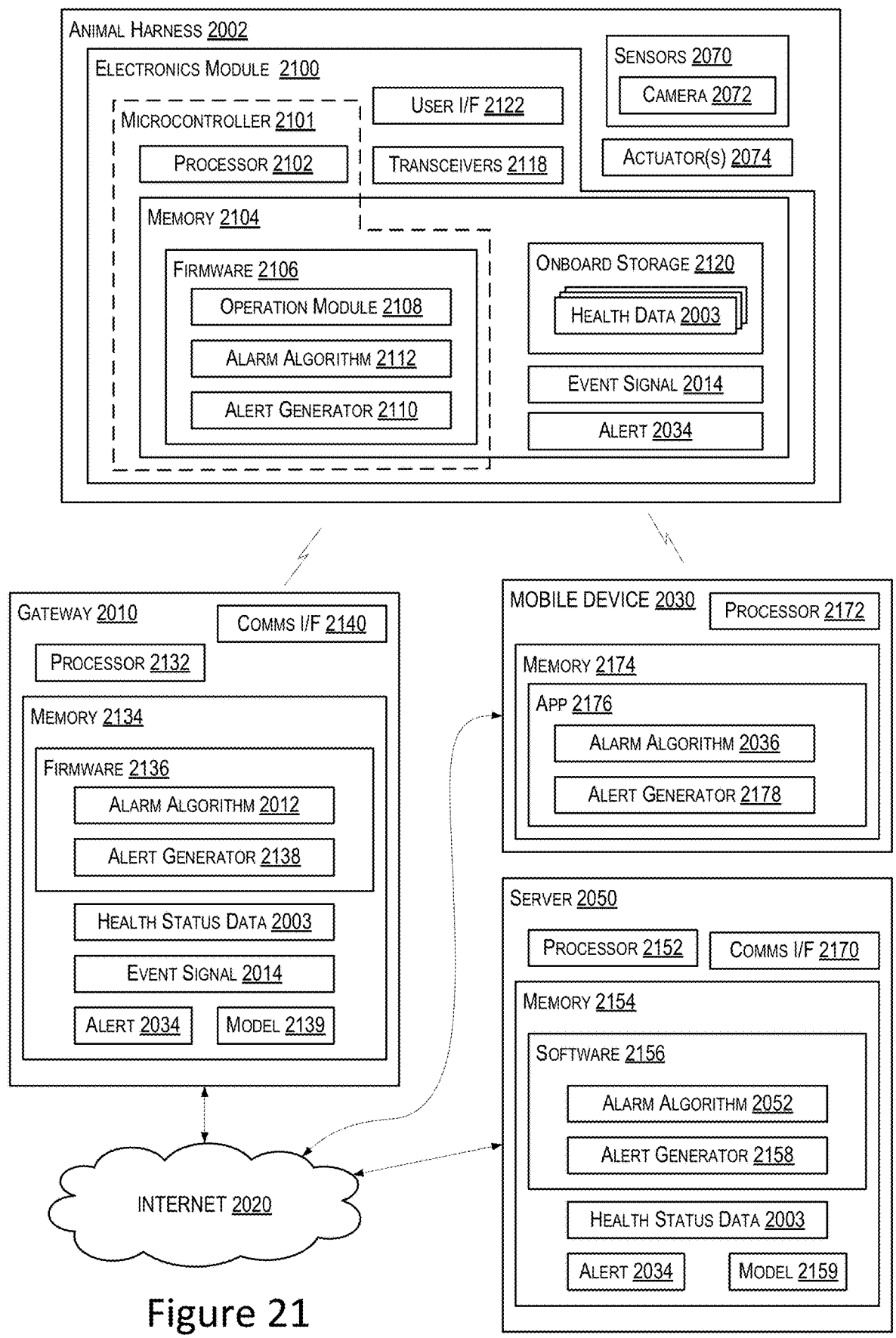
FIG. 21 is a block diagram illustrating the system of FIG. 20, and showing example detail of an electronics module of the animal harness, example detail of the gateway, example detail of the mobile device, and example detail of the server, in embodiments.

FIG. 21 is a block diagram illustrating system 2000 of FIG. 20, and showing example detail of an electronics module 2100 of animal harness 2002, example detail of gateway 2010, example detail of mobile device 2030, and example detail of server 2050. Electronics module 2100 may include functionality similar to electronics module 406 of FIG. 17. However, for clarity of illustration, electronics module 2100 is shown only with a processor 2102, memory 2104, a transceiver 2118, and a user interface 2122. Transceiver 2118 may implement one or more protocols (e.g., Wi-Fi, WiMAX, cellular, Z-wave, Bluetooth, and so on) for communicating with gateway 2010. Processor 2102 and at least part of memory 2104 may be implemented as a microcontroller 2101. Memory 2104 includes firmware 2106, having machine-readable instructions that, when executed by processor 2102, implement an operation module 2108 that, similar to operation module 1708, captures health status data 2003 from sensors 2070 of animal harness 2002, and stores health status data 2003 in onboard storage 2120. Electronics module 2100 may include a user interface 2122 that is similar to user interface 222 of FIG. 2, that a user may use to configure and interact with animal harness 2002. Further, when mobile device 2030 is within wireless range of animal harness 2002, such as when animal harness 2002 and mobile phone 2030 are wirelessly connected by Bluetooth (e.g., BLE), app 2176 may all mobile device 2030 to operates as the user interface for animal harness 2002 to allow a user to configure and control functionality of animal harness 2002. In certain embodiments, user interface 2122 may be omitted from animal harness 2002, wherein app 2176 running on mobile device 2030 communicates with electronics module 2100, via transceiver 2118, to allow a user to configure animal harness 2002.

In certain embodiments, operation module 2108 sends heath status data 2003 to gateway 2010, using transceivers 2118. In other embodiments, firmware 2106 includes alarm algorithm 2112 that process health status data 2003 to determine when event 2008 is witnessed by animal 2004 and an alert generator 2110 that, in response to alarm algorithm 2112 detecting event 2008 in health status data 2003, generates and sends, directly and/or via gateway 2010, event signal 2014 to security apparatus 2060. For example, alarm algorithm 2112 may detect one or more of excitement, agitation, stress, and anxiety in animal 2004 that indicates that animal 2004 is witnessing event 2008. Alert generator 2110 may also generate and send, via gateway 2010, alert 2034 to mobile device 2030.

Gateway 2010 is shown with a processor 2132, memory 2134, and a communication interface 2140. Communication interface 2140 may implement one or more protocols (e.g., Wi-Fi, WiMAX, cellular, Z-wave, Bluetooth, and so on) for communicating with electronics module 2100 and may include a wired and/or wireless connection to Internet 2020. Memory 2134 includes firmware 2136 with machine readable instructions that, when executed by processor 2132, implement functionality of gateway 2010 to provide connectivity with Internet 2020. For example, in certain embodiments, gateway 2010 receives health status data 2003 from electronics module 2100 and sends health status data 2003 to server 2050.

In certain embodiments, firmware 2136 may also include alarm algorithms 2012 that process health status data 2003, received from electronics module 2100, to determine an indication of event 2008. Firmware 2136 may also include an alert generator 2138 that generates and sends event signal 2014 to security apparatus 2060 and may also generate and send alert 2034 to mobile device 2030.

Server 2050 includes at least one processor 2152, memory 2154, and a communication interface 2170. Memory 2154 stores software 2156 that includes machine readable instructions that, when executed by the at least one processor 2152 cause server 2050 to receive, via gateway 2010, health status data 2003 from animal harness 2002. Software 2156 may implement alarm algorithms 2052 that control processor 2152 to process health status data 2003, received from electronics module 2100, to determine an indication of event 2008. Software 2156 may also include an alert generator 2158 that generates and sends alert 2034 to mobile device 2030 when health status data 2003 is determined to indicate event 2008.

Figure 22:
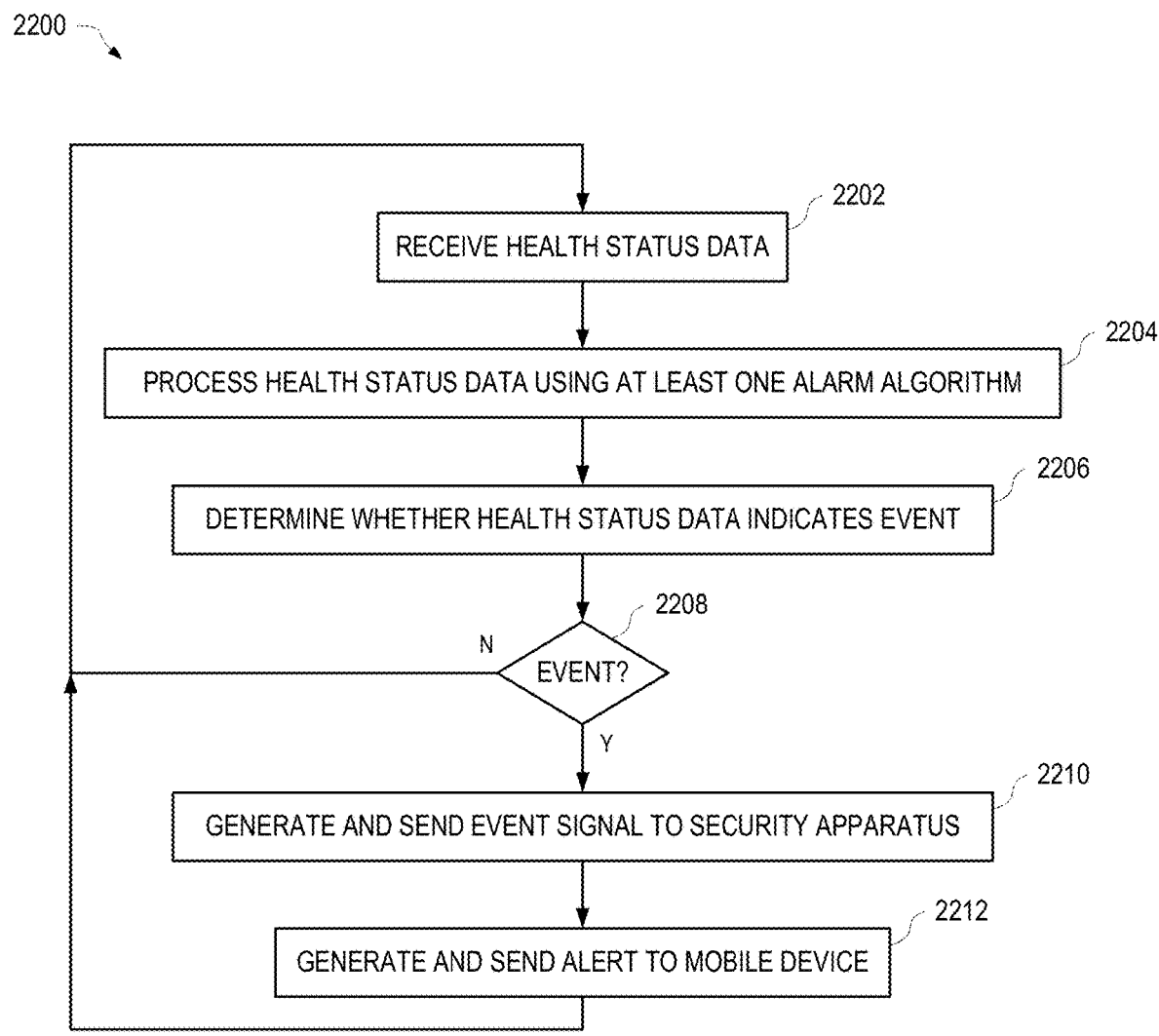
FIG. 22 is a flowchart illustrating one example method for animal harness security, in embodiments.

FIG. 22 is a flowchart illustrating one example method 2200 for animal harness security. Method 2200 may be implemented within firmware 2136 of gateway 2010, software 2156 of server 2050, and/or app 2176 of mobile device 2030. In block 2202, method 2200 receives health status data from an animal harness. In one example of block 2202, firmware 2136 receives, via communication interface 2140, health status data 2003 from electronics module 2100 of animal harness 2002. In block 2204, method 2200 processes the health status data using at least one alarm algorithm. In one example of block 2204, firmware 2136 invokes alarm algorithms 2012 to process health status data 2003. In block 2206, method 2200 determines whether the health status data indicates an event. In one example of block 2206, alert generator 2138 evaluates output from alarm algorithms 2012 to determine whether health status data 2003 indicates that animal 2004 is witnessing event 2008. Block 2208 is a decision. If, in block 2208, method 2200 determines that the health status data indicates an event, method 2200 continues with block 2210; otherwise, method 2200 continues with block 2202. Blocks 2202 through 2208 repeat to process health status data as it is received.

In block 2210, method 2200 generates and sends an event signal to a security apparatus. In one example of block 2210, alert generator 2138 generates event signal 2014 and sends event signal 2014 to security apparatus 2060. In certain embodiments, event signal 2014 indicates a probability, based upon processing of health status data 2003, of event 2008 being detected correctly. In block 2212, method 2200 generates and sends an alert to a mobile device. In one example of block 2212, alert generator 2138 generates alert 2034 with details (e.g., time, location, type of event, and probability that event rally occurred) of event 2008 determined from health status data 2003 to mobile device 2030, thereby notifying user 2040 of event 2008.

Advantageously, by using animal harness 2002 to collect health status data 2003 from animal 2004 at location 2006, and by using alarm algorithms 2012 to process health status data 2003 and determine whether health status data 2003 indicates one or more of excitement, agitation, stress, anxiety, etc., system 2000 may determine whether animal 2004 is witnessing event 2008 and may generate an alarm signal for security apparatus 2060 and may generate alert 2034 (e.g., a notification) on mobile device 2030 to make user 2040 aware of event 2008. Particularly, through use of harness 2002 as an IoT device, alarm algorithms 2012 and/or 2052 receive animal health status data that may be processed to derive security data.

In certain embodiments, where animal 2004 and animal harness 2002 cooperate with security apparatus 2060 to protect location 2006, animal 2004 may be trained to respond to certain signals from the security apparatus 2060. In these embodiments, animal harness 2002 includes one or more actuators 2074 that stimulate animal 2004 in response to a signal 2068 from security apparatus 2060. Actuators 2074 may include a vibrator and/or an audio output that stimulates animal 2004 using one or both of vibrations and/or sounds, and animal 2004 may be trained with certain responses to different vibrations and/or sounds. One or both of security apparatus 2060 and mobile device 2030 (or an associated server thereof) may include an algorithm (e.g., AI) that evaluates events detected by security apparatus 2060 and/or animal harness 2002 to determine an appropriate action for animal 2004, and cause security apparatus 2060 to send signal 2068 to animal harness 2002 to instruct animal 2004 to take that action. In another example, a user of mobile device 2030, upon receiving alert 2034 may control mobile device 2030 to generate and send signal 2068 to animal harness 2002. In another example, after viewing video and/or still images and/or hearing captured audio from camera 2072 on mobile device 2030, the user may instruct mobile device 2030 to generate and send signal 2068 to animal harness 2002 to instruct animal 2004 with certain behavior (e.g., down, heel, attack, etc).

Signal 2068 may be received at animal harness 2002 via gateway 2010, or directly from security apparatus 2060 and/or mobile device 2030. In certain embodiments, signal 2068 is sent to animal harness 2002 via security sensor 2064, such as when animal 2004 is near security sensor 2064.

In one example of operation, security apparatus 2060 is triggered by an external sensor (not shown) and sends signal 2068 to animal harness 2002 to cause actuator 2074 to stimulate animal 2004, which in response barks and moves around internal space 2007. In another example of operation, the user receives alert 2034 on mobile device 2030, and uses mobile device 2030 to send signal 2068 to instruct animal 2004 to lie down and remain quiet. In another example of operation, server 2050 receives health data 2003 from animal harness 2002 and alarm algorithm 2052 determine that health status data 2003 indicates one or more of excitement, agitation, stress, anxiety, etc., system 2000 may determine that animal 2004 is witnessing event 2008, generates alert 2034, and automatically sends signal 2068 to animal harness 2002 to instruct animal 2004 to lie down.

Changes may be made in the above system, methods or devices without departing from the scope hereof. For example, although described for use with animals, the harness may also be constructed for use with humans. It should thus be noted that the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall therebetween.

What is claimed is:
1. An animal harness security system, comprising:
an animal harness comprising:
   an electronics module with at least one first processor, first memory storing firmware, and a wireless transceiver;
   a plurality of sensors;
   at least one flexible panel electrically coupling the plurality of sensors to the electronics module;
   a soft chassis having a main body with a cavity for containing and positioning the flexible panel around a heart girth of an animal, wherein the soft chassis positions the sensors around the animal to detect health characteristics of the animal;
   at least three snap connectors, a female side of each one of the three snap connectors being attached to a different one of three removable ECG electrodes, and a male side of each one of the three snap connectors being attached through one of three holes in the flexible panel and electrically connected, through the flexible panel, to the electronics module, wherein each of the three snap connectors are assembled through three holes in the soft chassis to position the three removable ECG electrodes at a left side of the animal, a right side of the animal, and on a back of the animal; and
   a plurality of snap fasteners attached to opposite sides of the soft chassis within the cavity, wherein each snap fastener couples together through a different hole within the flexible panel to secure the flexible panel with the soft chassis; and a server comprising:
- at least one second processor; and
- a second memory storing machine readable instructions that, when executed by the at least one second processor, cause the at least one second processor to:
  - receive, at intervals, health status data from the animal harness;
  - determine whether the health status data indicates that the animal is witnessing a security event; and
  - generating an alarm signal to indicate the security event.

2. The animal harness security system of claim 1, the firmware comprising machine readable instructions that, when executed by the at least one first processor, cause the at least one first processor to:
- detect changes in at least one of excitement, agitation, stress, and anxiety in the health status data; and
- determine whether the animal is witnessing the security event based upon the changes in the at least one of excitement, agitation, stress, and anxiety.

3. The animal harness security system of claim 2, the firmware further comprising machine readable instructions that, when executed by the at least one first processor, cause the at least one first processor to generate the alarm signal to indicate the security event.

4. The animal harness security system of claim 3, the firmware further comprising machine readable instructions that, when executed by the at least one first processor, cause the at least one first processor to send a signal to a security apparatus.

5. The animal harness security system of claim 1, the second memory further comprising machine readable instructions that, when executed by the at least one second processor, cause the at least one second processor to:
- detect changes in at least one of excitement, agitation, stress, and anxiety in the health status data; and
- determine whether the animal is witnessing the security event based upon the changes in the at least one of excitement, agitation, stress, and anxiety.

6. The animal harness security system of claim 5, the second memory further comprising machine readable instructions that, when executed by the at least one second processor, cause the at least one second processor to:
- implement a behavioral model for the animal based upon excitement, agitation, stress, and anxiety; and
- use the behavioral model to determine whether the changes in the at least one of excitement, agitation, stress, and anxiety indicate that the animal is witnessing the security event.

7. The animal harness security system of claim 1, the soft chassis further comprising two axillary straps, each positioned towards an opposite end of the soft chassis and each being partially hollow to receive an offshoot of the flexible panel having at least one of the sensors attached thereto, the two axillary straps forcing the sensors against axillary areas of the animal.

8. The animal harness security system of claim 1, the plurality of sensors including one or more of a temperature sensor, an auscultation sensor, an ECG sensor, a movement sensor, an ambient temperature sensor, and an ambient humidity sensor.

9. A method for detecting a security event witnessed by an animal, comprising:
- capturing, at intervals, from a plurality of sensors positioned on the animal by an animal harness worn by the animal, health status data of the animal;
- processing the health status data to detect changes in at least one of excitement, agitation, stress, and anxiety in the animal;
- interpreting the changes in the at least one of excitement, agitation, stress, and anxiety to determine whether the animal is witnessing the security event;
- sending an event signal indicative of the security event to a security apparatus when the animal is witnessing the security event;
- receiving an enquiry signal from a triggered security sensor of the security apparatus; and
- transmitting a coded signal in response to the enquiry signal;
- wherein a signal strength of the coded signal received by the triggered security sensor indicates a likelihood of the animal having triggered the triggered security sensor.

10. The method of claim 9, the health status data including one or more of ECG, pulse/heart rate, respiratory rate, animal temperature, animal movement, environmental temperature, and environmental humidity.

11. The method of claim 9, the processing the health status data further comprising:
- detecting patterns in the changes in the at least one of excitement, agitation, stress, and anxiety; and
- interpreting the patterns to determine whether the animal is witnessing the security event.

12. The method of claim 9, further comprising:
- generating a behavioral model of the animal based upon the changes in the at least one of excitement, agitation, stress, and anxiety; and
- using the behavioral model to relate the changes in the at least one of excitement, agitation, stress, and anxiety in the animal to events that the animal is witnessing.

* * * * *